(12) United States Patent
Davies et al.

(10) Patent No.: US 11,565,021 B1
(45) Date of Patent: Jan. 31, 2023

(54) COMPOSITE STRUCTURE POROUS IMPLANT FOR REPLACING BONE STOCK

(71) Applicant: ORTHO DEVELOPMENT CORPORATION, Draper, UT (US)

(72) Inventors: Bryan K Davies, Taylorsville, UT (US); Alfred S Despres, Heber City, UT (US); Susanne F Sealy, Draper, UT (US); Cass K Nakasone, Honolulu, HI (US); Anthony P Sanders, Sandy, UT (US); Bao-Khang Ngoc Nguyen, Salt Lake City, UT (US)

(73) Assignee: ORTHO DEVELOPMENT CORPORATION, Draper, UT (US)

( * ) Notice: Subject to any disclaimer, the term of this patent is extended or adjusted under 35 U.S.C. 154(b) by 359 days.

(21) Appl. No.: 16/674,792

(22) Filed: Nov. 5, 2019

Related U.S. Application Data

(63) Continuation-in-part of application No. 29/701,487, filed on Aug. 12, 2019, now Pat. No. Des. 901,013, and a continuation-in-part of application No. 29/701,478, filed on Aug. 12, 2019, now Pat. No. Des. 901,012, and a continuation-in-part of application No. 29/701,489, filed on Aug. 12, 2019, now Pat. No. Des. 901,014.

(51) Int. Cl.
| | |
|---|---|
| *A61L 27/06* | (2006.01) |
| *A61F 2/00* | (2006.01) |
| *A61L 27/56* | (2006.01) |
| *A61F 2/30* | (2006.01) |

(52) U.S. Cl.
CPC ............ *A61L 27/06* (2013.01); *A61F 2/0077* (2013.01); *A61L 27/56* (2013.01); *A61F 2002/0086* (2013.01); *A61F 2002/3093* (2013.01); *A61L 2400/18* (2013.01); *A61L 2430/02* (2013.01)

(58) Field of Classification Search
CPC combination set(s) only.
See application file for complete search history.

(56) References Cited

U.S. PATENT DOCUMENTS

| | | |
|---|---|---|
| 3,906,550 A | 9/1975 | Rostoker |
| 4,224,696 A | 9/1980 | Murray |
| 4,550,448 A | 11/1985 | Kenna |
| 4,728,335 A | 3/1988 | Jurgutis |
| 4,735,625 A | 4/1988 | Davidson |
| 4,753,657 A | 6/1988 | Lee |
| 4,790,852 A | 12/1988 | Noiles |
| 4,834,756 A | 5/1989 | Kenna |

(Continued)

FOREIGN PATENT DOCUMENTS

WO    WO 2011/060312 A3    5/2011

OTHER PUBLICATIONS

Biomet, Vanguard 360 Revision Knee System Design Rationale, USA, 2012.

(Continued)

*Primary Examiner* — Yashita Sharma
(74) *Attorney, Agent, or Firm* — Brett Peterson

(57) ABSTRACT

A porous implant for repairing lost bone stock such as around a prosthetic joint is provided. The porous implant has a composite structure with a solid structure and a porous structure which may be formed monolithically by direct metal laser sintering. The solid structure includes a support structure which extends into the porous structure.

29 Claims, 26 Drawing Sheets

(56) References Cited

U.S. PATENT DOCUMENTS

| | | | | |
|---|---|---|---|---|
| 4,840,632 | A | 6/1989 | Kampner | |
| 4,865,607 | A | 9/1989 | Witzel | |
| 4,944,757 | A | 7/1990 | Martinez | |
| 4,944,760 | A | 7/1990 | Kenna | |
| 5,019,103 | A | 5/1991 | Van Zile | |
| 5,026,373 | A * | 6/1991 | Ray | A61B 17/1637 606/279 |
| 5,035,713 | A | 7/1991 | Friis | |
| 5,037,423 | A | 8/1991 | Kenna | |
| 5,057,101 | A | 10/1991 | Dorr | |
| 5,192,324 | A | 3/1993 | Kenna | |
| 5,441,537 | A | 8/1995 | Kenna | |
| 5,462,563 | A | 10/1995 | Shearer | |
| 5,591,233 | A | 1/1997 | Kelman | |
| 5,697,932 | A | 12/1997 | Smith | |
| 5,734,959 | A | 3/1998 | Krebs | |
| 5,824,103 | A | 10/1998 | Williams | |
| 5,879,398 | A | 3/1999 | Swarts | |
| 5,958,314 | A | 9/1999 | Draenert | |
| 5,997,581 | A | 12/1999 | Khalili | |
| 6,008,432 | A | 12/1999 | Taylor | |
| 6,049,054 | A * | 4/2000 | Panchison | A61F 2/30907 219/121.64 |
| 6,071,311 | A | 6/2000 | O'Neil | |
| 6,117,175 | A | 9/2000 | Bosredon | |
| 6,136,029 | A | 10/2000 | Johnson | |
| 6,139,584 | A | 10/2000 | Ochoa | |
| 6,156,070 | A | 12/2000 | Incavo | |
| 6,214,053 | B1 | 4/2001 | Ling | |
| 6,264,699 | B1 | 7/2001 | Noiles | |
| 6,432,141 | B1 | 8/2002 | Stocks | |
| 6,464,728 | B1 | 10/2002 | Murray | |
| 6,626,950 | B2 * | 9/2003 | Brown | A61L 27/425 623/23.72 |
| 6,645,206 | B1 * | 11/2003 | Zdeblick | A61F 2/4637 606/86 R |
| 6,692,531 | B1 | 2/2004 | Yoon | |
| 6,767,369 | B2 | 7/2004 | Boyer | |
| 6,843,806 | B2 | 1/2005 | Hayes | |
| 6,863,692 | B2 | 3/2005 | Meulink | |
| 6,974,483 | B2 | 12/2005 | Murray | |
| 6,981,991 | B2 | 1/2006 | Ferree | |
| 7,044,977 | B2 | 5/2006 | Ferree | |
| 7,115,146 | B2 | 10/2006 | Boyer | |
| 7,182,786 | B2 | 2/2007 | Justin | |
| D538,431 | S | 3/2007 | Botha | |
| 7,291,174 | B2 | 11/2007 | German | |
| 7,323,013 | B2 | 1/2008 | McTighe | |
| 7,491,242 | B2 | 2/2009 | Pichon | |
| 7,575,603 | B2 | 8/2009 | Bergin | |
| D618,800 | S | 6/2010 | Mayon | |
| 7,799,085 | B2 | 9/2010 | Goodfried | |
| 7,799,086 | B2 | 9/2010 | Justin | |
| 7,806,936 | B2 | 10/2010 | Wright | |
| 7,857,858 | B2 | 12/2010 | Justin | |
| 7,892,288 | B2 | 2/2011 | Blaylock | |
| 7,892,290 | B2 | 2/2011 | Bergin | |
| 8,075,628 | B2 | 12/2011 | Justin | |
| 8,187,336 | B2 | 5/2012 | Jamali | |
| 8,241,357 | B2 | 8/2012 | Bhatnagar | |
| 8,241,367 | B2 | 8/2012 | Justin | |
| 8,268,007 | B2 | 9/2012 | Barsoum | |
| 8,292,967 | B2 * | 10/2012 | Brown | A61F 2/30907 623/23.19 |
| 8,382,849 | B2 | 3/2013 | Thomas | |
| 8,424,183 | B2 | 4/2013 | Thomas | |
| 8,444,699 | B2 | 5/2013 | Metzger | |
| D684,693 | S | 6/2013 | Hanssen | |
| 8,506,645 | B2 | 8/2013 | Blaylock | |
| 8,535,385 | B2 | 9/2013 | Hanssen | |
| 8,535,386 | B2 | 9/2013 | Servido | |
| 8,585,770 | B2 | 11/2013 | Meridew | |
| 8,641,773 | B2 | 2/2014 | Bergin | |
| 8,679,166 | B2 | 3/2014 | Bhatnagar | |
| 8,721,733 | B2 | 5/2014 | Bonitati | |
| 8,728,168 | B2 | 5/2014 | Hanssen | |
| 8,876,909 | B2 | 11/2014 | Meridew | |
| 8,900,311 | B2 * | 12/2014 | Ciupik | A61F 2/4465 623/17.16 |
| 8,900,317 | B2 | 12/2014 | Zubok | |
| 8,926,708 | B2 | 1/2015 | Servido | |
| 8,932,364 | B2 | 1/2015 | Mooradian | |
| 8,968,415 | B2 | 3/2015 | Meridew | |
| 9,044,326 | B2 | 6/2015 | Blaylock | |
| 9,161,840 | B2 | 10/2015 | Hayes | |
| 9,241,801 | B1 | 1/2016 | Parry | |
| 9,265,614 | B2 | 2/2016 | Blaylock | |
| 9,289,299 | B2 | 3/2016 | Metzger | |
| 9,517,138 | B2 | 12/2016 | Zubok | |
| 9,539,096 | B2 | 1/2017 | Hanssen | |
| 9,668,870 | B2 | 6/2017 | Wasielewski | |
| 9,713,532 | B2 | 7/2017 | Blaylock | |
| 9,744,047 | B2 | 8/2017 | Meridew | |
| 9,907,664 | B2 | 3/2018 | Blaylock | |
| D847,338 | S | 4/2019 | Arabin | |
| D875,936 | S | 2/2020 | Martin | |
| 10,736,752 | B1 * | 8/2020 | Schifano | A61F 2/4465 |
| 2001/0004712 | A1 | 6/2001 | Sydney | |
| 2001/0039456 | A1 | 11/2001 | Boyer | |
| 2002/0045949 | A1 | 4/2002 | Ling | |
| 2003/0065397 | A1 | 4/2003 | Hanssen | |
| 2003/0130740 | A1 | 7/2003 | Stocks | |
| 2003/0153981 | A1 | 8/2003 | Wang | |
| 2004/0049285 | A1 | 3/2004 | Haas | |
| 2004/0162619 | A1 | 8/2004 | Blaylock | |
| 2005/0010304 | A1 | 1/2005 | Jamali | |
| 2005/0283254 | A1 | 12/2005 | Hayes | |
| 2006/0147332 | A1 | 7/2006 | Jones | |
| 2006/0229734 | A1 | 10/2006 | Yoon | |
| 2007/0088443 | A1 | 4/2007 | Hanssen | |
| 2008/0195218 | A1 | 8/2008 | Jones | |
| 2010/0114323 | A1 | 5/2010 | Deruntz | |
| 2010/0145452 | A1 | 6/2010 | Blaylock | |
| 2010/0222891 | A1 | 9/2010 | Goodfried | |
| 2012/0059484 | A1 | 3/2012 | Justin | |
| 2012/0215311 | A1 | 8/2012 | Parry | |
| 2012/0321878 | A1 | 12/2012 | Landon | |
| 2013/0013078 | A1 | 1/2013 | Hanssen | |
| 2013/0013080 | A1 | 1/2013 | Hanssen | |
| 2013/0018478 | A1 | 1/2013 | Hanssen | |
| 2013/0274886 | A1 * | 10/2013 | Matsumoto | A61F 2/442 623/17.16 |
| 2014/0081418 | A1 | 3/2014 | Hanssen | |
| 2014/0249637 | A1 | 9/2014 | Hanssen | |
| 2014/0277534 | A1 | 9/2014 | Wasielewski | |
| 2015/0257890 | A1 | 9/2015 | Blaylock | |
| 2016/0058560 | A1 | 3/2016 | Blaylock | |
| 2016/0193049 | A1 | 7/2016 | McTigue | |
| 2017/0020675 | A1 | 1/2017 | Blaylock | |
| 2017/0333195 | A1 | 11/2017 | Wasielewski | |
| 2018/0098856 | A1 | 4/2018 | Blaylock | |

OTHER PUBLICATIONS

Depuy, Knee Revision Product Portfolio, USA, 2009.
Depuy, Gription TF Acetabular Augments, USA, 2013.
Depuy, Sigma LCS Revision Brochure, USA, 2006.
Gross, Allografts in Orthopaedic Practice, p. 184, Williams & Wilkins, Baltimore USA, 1992.
Mnaymneh, Massive Allografts in Salvage Revisions of Failed Total Knee Arthroplasties, Clinical Orthopedics, Nov. 1990, pp. 144-153, No. 260.
Zimmer, Trabecular Metal Femoral and Tibial Cone Augments, USA, 2008.

* cited by examiner

COMPOSITE STRUCTURE POROUS IMPLANT FOR REPLACING BONE STOCK

THE FIELD OF THE INVENTION

The present invention relates to medical implants. In particular, examples of the present invention relates to a device for restoring lost bone stock at a prosthetic joint implant site.

BACKGROUND

Numerous prosthetic joints have been developed to replace damaged joints. Replacement of knee and hip joints, for example, is common in elderly people and in people whose joints have become damaged through sports or trauma. Primary prosthetic joints can wear out or otherwise fail due to age or trauma and need to be replaced. Replacement of a primary prosthetic joint with a second prosthetic joint may occur during a revision surgery. In each of these instances, a surgeon may encounter damage to the bone surrounding the joint.

BRIEF DESCRIPTION OF THE DRAWINGS

Non-limiting and non-exhaustive examples of the present invention are described with reference to the following figures, wherein like reference numerals refer to like parts throughout the various views unless otherwise specified.

Figure 1:
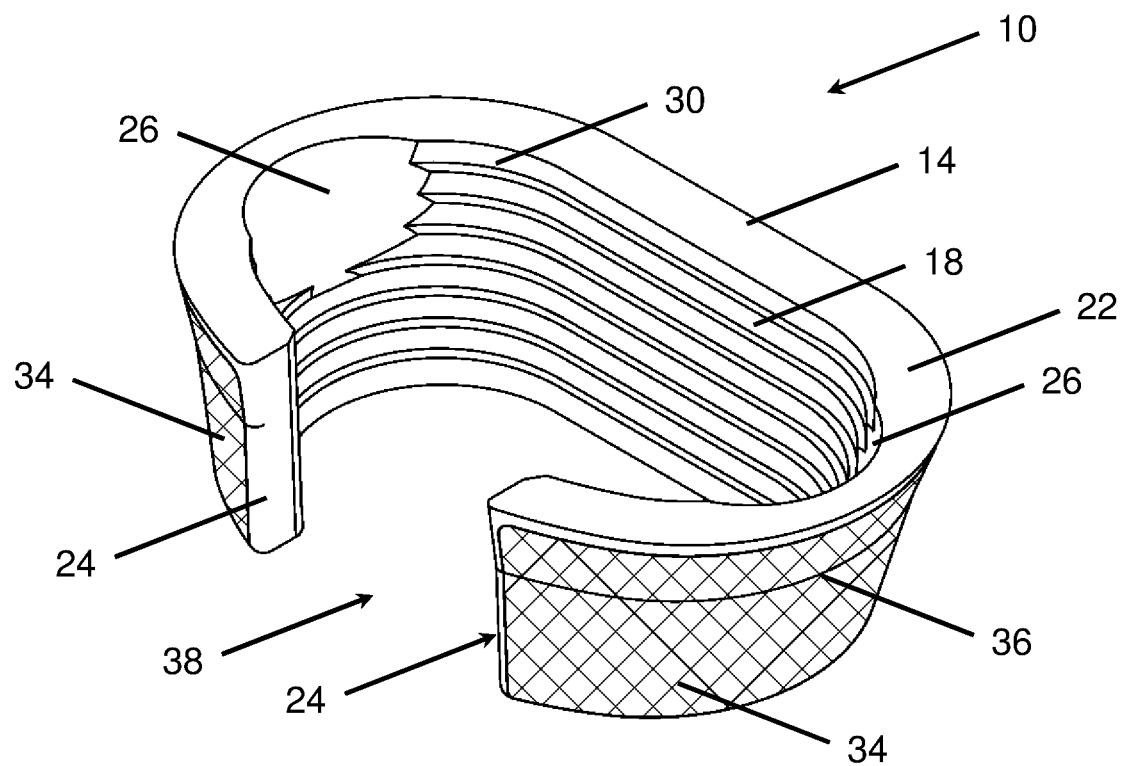
FIG. 1 is a drawing which shows a porous implant.

Corresponding reference characters indicate corresponding components throughout the several views of the drawings. Unless otherwise noted, the drawings have been drawn to scale. Skilled artisans will appreciate that elements in the figures are illustrated for simplicity and clarity. For example, the dimensions of some of the elements in the figures may be exaggerated relative to other elements to help improve understanding of various examples of the present invention. Also, common but well-understood elements that are useful or necessary in a commercially feasible embodiment are often not depicted in order to facilitate a less obstructed view of these various embodiments of the present invention.

It will be appreciated that the drawings are illustrative and not limiting of the scope of the invention which is defined by the appended claims. The examples shown each accomplish various different advantages. It is appreciated that it is not possible to clearly show each element or advantage in a single figure, and as such, multiple figures are presented to separately illustrate the various details of the examples in greater clarity. Similarly, not every example need accomplish all advantages of the present disclosure.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

In the above disclosure, reference has been made to the accompanying drawings, which form a part hereof, and in which are shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, such feature, structure, or characteristic may be used in connection with other embodiments whether or not explicitly described. The particular features, structures or characteristics may be combined in any suitable combination and/or sub-combinations in one or more embodiments or examples. It is appreciated that the figures provided herewith are for explanation purposes to persons ordinarily skilled in the art.

As used herein, "adjacent" refers to near or close sufficient to achieve a desired effect. Although direct contact is common, adjacent can broadly allow for spaced apart features.

As used herein, the singular forms "a," and, "the" include plural referents unless the context clearly dictates otherwise.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a number or numerical range endpoint by providing that a given value may be "a little above" or "a little below" the number or endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Dimensions, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

The disclosure particularly describes a porous implant for restoring lost bone stock in skeletal applications such as around a prosthetic joint. Particularly, the present disclosure describes a composite structure porous implant which combines both solid structures and porous structures within the overall volume of the implant in order to provide a device which achieves high strength and which also integrates well with native bone. The structure of the device allows the device to be manufactured with additive manufacturing and reduces the cost of manufacturing the device.

Significant challenges exist in installing prosthetic joints in patients. One challenge is the variable condition of the patient bone encountered during a surgery. Some patients need an artificial joint due to degradation of the soft tissue within a joint. In such a situation, the bone itself may be relatively undamaged and the surgery to install an artificial joint may proceed without significant complication. Other patients present damage or degradation of the bone surrounding the joint. In such a situation, the natural bone may provide insufficient physical support for installing an artificial joint and providing for long term success of that joint. In these situations, it is beneficial to provide additional mechanical support for the joint. Some patients have an existing artificial joint which has failed or outlived its useful life and needs replacement. In this situation, removal of the artificial joint during a revision surgery may necessitate removal of additional damaged bone stock or bone stock to which the primary artificial joint was attached. Removal of additional bone stock may leave insufficient bone stock to support the revision joint. If the primary joint failed due to failure of the attachment of the joint to the patient bone, the patient often presents an amount of degraded bone tissue around the primary joint which must be removed or strengthened before installing the revision joint. In each of these situations a surgeon may be presented with a variable quantity and quality of natural bone to work with while installing an artificial joint. The present invention provides a device to repair and reinforce damaged bone stock. The device allows for flexible installation by a surgeon to address the variable nature of patient bone during a surgery.

Another issue present with prosthetic joints involves stress shielding and the design of the artificial joint. Bone is a living tissue which responds to the stresses placed upon it. Bone includes an outer layer of cortical bone which is dense and provides a majority of the bone's strength and an inner section of cancellous bone which is softer and highly porous. If an artificial joint does not place stress on a section of bone which traditionally carried stress, that section of bone may atrophy and degrade. Because of this, it may be desirable to attach an artificial joint to the cortical bone near the original joint space so that the bone is loaded in a similar manner as when the natural joint was present. Traditional revision joints in particular may address the further removal or degradation of natural bone by providing a lengthy stem which anchors the joint to the bone medullary cavity via cement. This joint design tends to shift stress from the portion of the bone adjacent the joint to the bone diaphysis and may result in gradual atrophy of the bone epiphysis or metaphysis. The present invention may allow a surgeon to preserve structural strength in the end of the bone adjacent the joint space and may allow the surgeon to use an artificial joint which attaches structurally to the bone near the original joint space; preserving a more natural transfer of stress from the joint to the bone.

The present invention provides several examples of a porous implant for replacing lost bone stock at a prosthetic joint. The example porous implants have overall shapes which are particularly useful in replacing lost bone stock near the end of a long bone, such as at a knee joint. The example porous implants include a composite structure which has both a solid structure and a porous structure which are joined together to form the overall implant. The solid structure provides strength to the porous implant and allows the porous implant to give good support to a prosthetic joint. The porous structure provides increased elasticity and allows the porous implant to interface with cancellous and cortical bone in a manner which minimizes stress at the bone/implant interface by minimizing strength and elasticity differences between the implant and the bone and provides an improved surface for bone ingrowth.

The example porous implants also provide structures which may be successfully manufactured using additive manufacturing techniques such as through electron beam or laser sintering/melting of metal powder. These manufacturing techniques are encompassed within powder bed fusion manufacturing where an energy beam such as a laser or electron beam is used to melt powder layer-by-layer in a bed to create the part. Laser sintering of titanium powder is given herein as an example method of manufacturing the porous implants 10 but it is understood that the parts could be manufactured by other powder bed fusion techniques such as electron beam sintering. The solid structure includes a support structure which engages/interfaces with the porous structure and which provides a surface that reduces the amount of internal stress present in the porous implant during sintering. The interface between the solid structure and the porous structure is shaped to significantly reduced stress in the porous implant and allow the porous implant to be laser sintered from titanium powder without experiencing problems such as cracking, warping, and spontaneously popping off of the build plate during sintering. Due to this, the porous implant may be manufactured with less expense and with a significantly reduced rate of defective parts.

Figure 26:
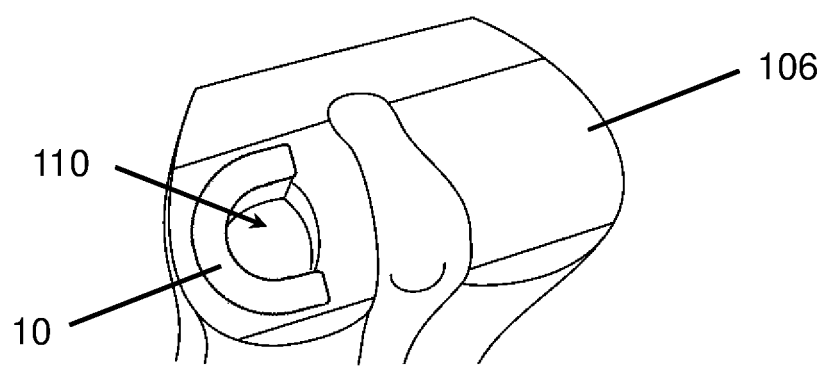
FIG. 26 is a drawing showing an example use of a porous implant.

Turning now to FIGS. 1 through 7, an example porous implant 10 for replacing lost bone stock is shown. FIG. 1 shows a perspective view of the example porous implant 10. The example porous implant 10 is particularly shaped for use in tibial replacement surgery or tibial joint revision surgery and is designed to fit in varying locations within the proximal epiphysis of a resected tibia. The porous implant 10 fits within the proximal tibia to reinforce cancellous bone and to strengthen damaged cortical bone and thereby provide a stable supporting surface to allow a surgeon to implant an artificial tibial joint component. The porous implant 10 is designed so that the upper surface of the porous implant 10 may directly contact and support an implanted tibial component. The implant 10 may also be useful in remedying bone defect in other locations such as a femur as shown in FIG. 26.

The porous implant 10 (e.g. the overall structure or the body of the porous implant 10) includes a solid structure 14 which provides strength to the porous implant 10. In the example implant 10, the solid structure 14 is made from laser sintered titanium powder and is solid with a somewhat rough surface from the sintering process. The solid structure 14 forms the interior surface 18 and the upper surface 22 of the porous implant 10. The interior surface 18 forms a vertical wall that extends through the height of the implant 10 and is a load bearing wall to provide strength to the implant. The upper surface 22 is a horizontally oriented wall of approximately 1 mm thickness which extends across the top of the porous implant 10 and supports a prosthetic joint component. The solid structure 14 may also form the inwardly facing walls 24 at the front opening of the implant 10. The implant 10 is typically installed in the end of a patient long bone so that the upper surface 22 is coplanar with a resected surface of the bone. In this position, the upper surface 22 of the implant 10 may directly contact a lower facing surface of the artificial joint component to support the artificial joint component. In discussing the implant 10, directions such as upper and lower are made relative to the normal orientation of the implant 10 as shown in the drawings while the orientation of the implant 10 may vary when installed in a body.

The body of the porous implant 10 is bent/curved about one or more vertical bend axes and is generally "C" shaped when viewed from above. The example porous implant 10 includes a generally straight back wall, side walls which curve forwards and then inwards from the back wall, and a front opening between the two side walls. The oval interior opening of the implant 10 is not complementary in shape to an exterior shape of an artificial joint such as an artificial tibial joint in order to attach to the artificial joint. That is to say that the interior opening of the porous implant 10 does not have a size and shape such as a Morse taper socket or another shape which is a mating fit with a lower surface of an artificial joint component to attach the porous implant to the artificial joint component. The porous implant 10 is attached to a bone independent of an artificial joint component. The porous implant 10 may be moved relative to the final position of the artificial joint component during installation of the porous implant 10 and is not positioned in a fixed location relative to the artificial joint component. The interior of the porous implant 10 is formed with recesses 26 on the interior surfaces of the side walls which provide additional room for positioning an artificial joint component within the interior of the porous implant 10. The recesses 26 are concave in a horizontal direction and are angled outwardly in a vertical direction relative to the interior side wall of the porous implant 10 and may receive wings which extend between a lower surface and a stem of a joint component to allow greater room for positioning the joint component. The interior surface 18 of the porous implant 10 may also include steps or ridges 30. The ridges 30 improve cement adhesion for cementing a joint component to the porous implant 10 while installing the implant 10 and artificial joint component.

The porous implant 10 also includes a porous structure 34 which is illustrated in the drawings with cross hatching. In the example implant 10, the porous structure 34 is an open cell structure formed by a network of interconnected struts. In the example porous implants the struts are formed by laser sintering titanium powder in discrete Z height layers and this process introduces some curvature and irregularity in the struts even if the struts were modeled as straight before sintering. The cells are typically between about 0.1 mm and about 1 mm in size and are often about 0.7 mm in size. The struts are often about 0.2 mm in diameter. The struts may be between about 0.1 mm and about 0.8 mm in diameter. These dimensions result in a porous structure which is approximately 20 percent solid struts and about 80 percent open space. The porous structure 34 may often be between about 10 percent solid structure and about 30 percent solid structure with a corresponding volume of open space which is between about 90 percent and about 70 percent open space. The porous structure 34 also forms a significant part of the porous implant 10. In the example implant 10, the porous structure 34 forms about 65 percent of the overall implant 10 by volume. The porous structure 34 may often form between about 50 percent and about 90 percent of the overall implant by volume. This will often vary according to the overall size and wall thickness of the porous implant. The porous structure 34 and the solid structure 14 have a complementary shape at the interface between the solid structure 14 and the porous structure 34 so that the porous structure is joined to the solid structure without voids between the two other than the open cells formed throughout the porous structure 34. The porous structure 34 wraps around the exterior of the implant 10 so that nearly all of the exterior front, back, and sides of the implant 10 are formed by the porous structure 34. The porous structure 34 has a significantly reduced strength and stiffness as compared to the solid structure. Accordingly, the porous structure provides a strength and stiffness which is closer to that of bone and which reduces stress at the joint between the implant 10 and bone. The porous structure 34 also allows for bone ingrowth into the implant 10.

Figure 2:
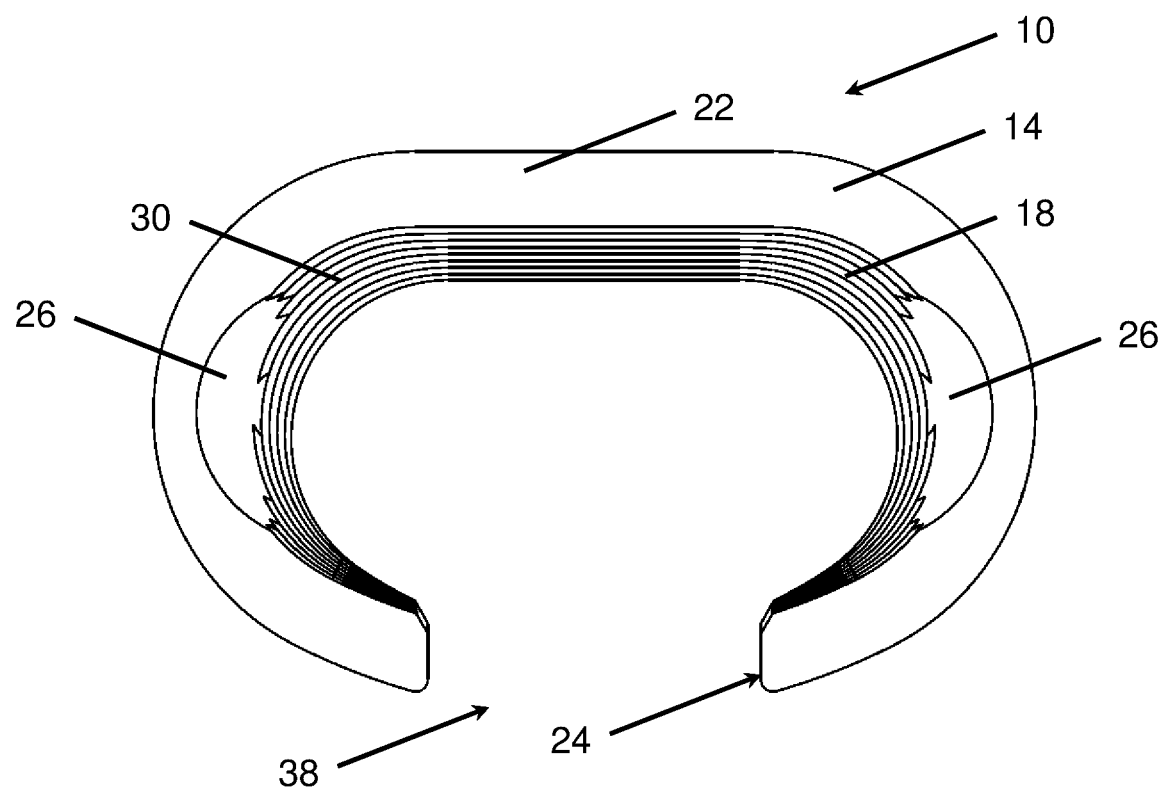
FIG. 2 is a drawing which shows the porous implant of FIG. 1.

FIG. 2 shows a top view of the implant 10. This drawing shows the "C" shape of the implant and the opening formed at the front of the implant 10. This drawing also illustrates the tapering shape of the implant 10. As can be seen from the inside surface of the implant, the implant tapers in size and is larger at the top than at the bottom. The implant 10 tapers in size on both the inside of the implant as well as on the outside of the implant. It can also be seen how the back and sides of the implant are angled inwardly and taper inwardly in dimension towards the bottom of the implant while the front ends of the implant adjacent the front opening 38 are nearly vertical and have little or no taper. The back and sides of the implant taper inwardly at an angle of about 15 degrees such that the sides and back are oriented at an angle of about 75 degrees to horizontal.

Figure 3:
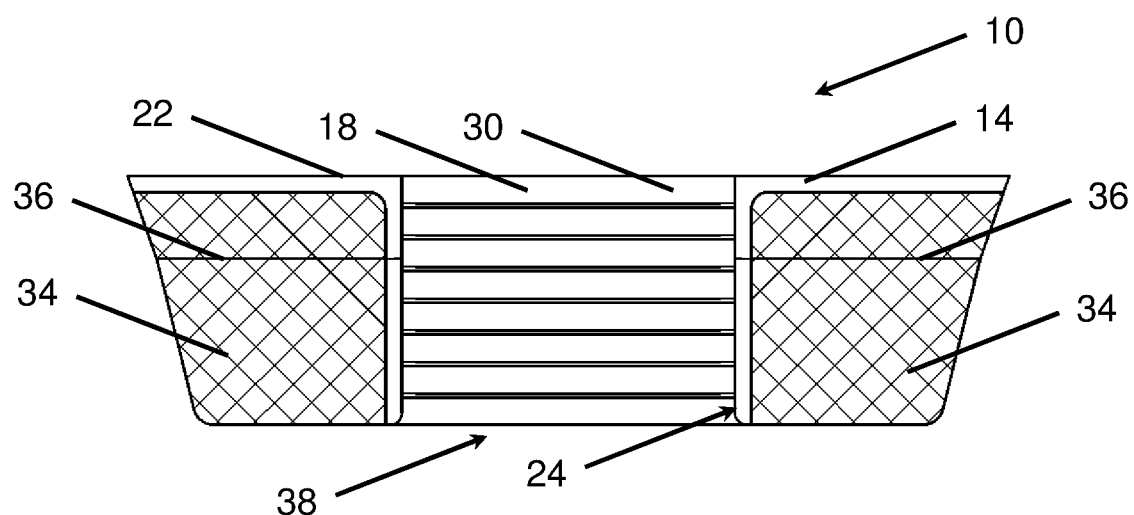
FIG. 3 is a drawing which shows the porous implant of FIG. 1.
Figure 4:
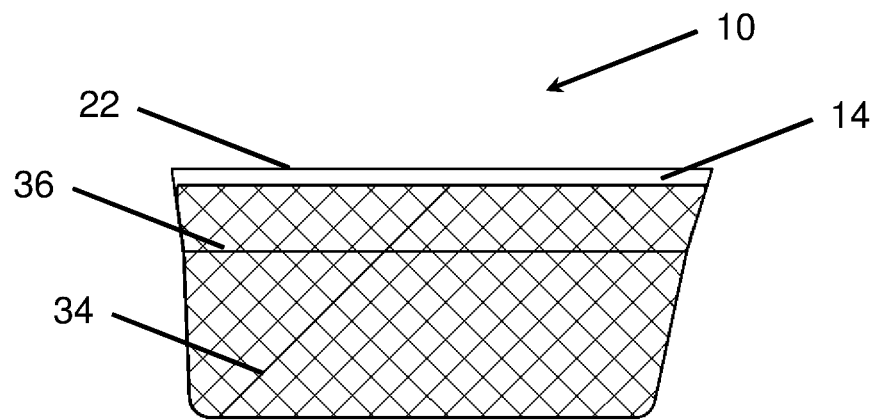
FIG. 4 is a drawing which shows the porous implant of FIG. 1.
Figure 5:
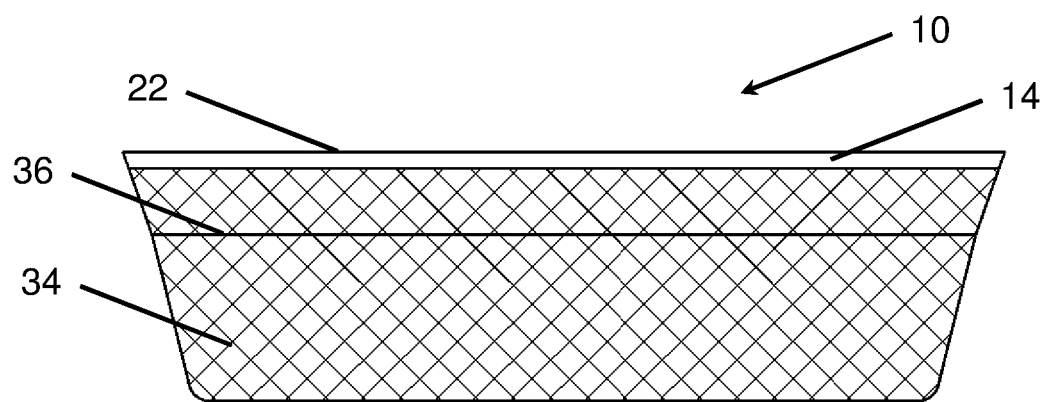
FIG. 5 is a drawing which shows the porous implant of FIG. 1.
Figure 6:
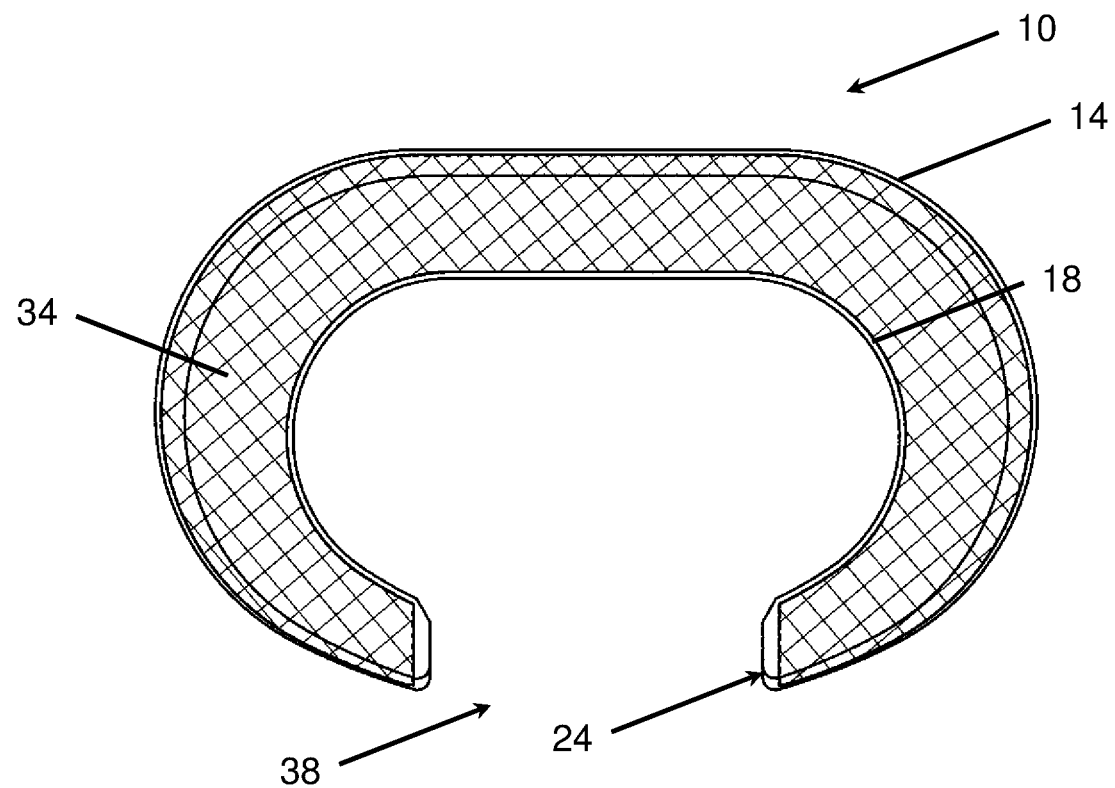
FIG. 6 is a drawing which shows the porous implant of FIG. 1.

FIG. 3 shows a front view of the implant 10, illustrating how the sides of the implant 10 taper inwardly more significantly while the front of the implant adjacent the front opening 38 tapers inwardly only very slightly. FIG. 4 shows a side view of the porous implant 10 and also shows how the back of the implant 10 tapers inwardly in size. The opposite side is symmetrical to the side shown. FIG. 5 shows a back view of the implant 10 and shows how the sides of the implant taper inwardly. It can also be seen how the porous structure 34 extends across the back of the implant 10. These drawings show how the exterior surface of the implant tapers inwardly towards the bottom of the implant. The exterior wall of the implant 10 is oriented at an angle of about 75 degrees relative to horizontal, or about 15 degrees relative to vertical. These drawings also show how the exterior surface of the implant 10 may be formed with a second taper angle on about the upper two thirds of the implant 10. Line 36 illustrates the horizontal height around the implant 10 where the taper angle of the exterior side wall increases by about 5 degrees. Accordingly, the exterior side wall is angled outwardly about 15 degrees from vertical below line 36 and is angled outwardly about 20 degrees from vertical above the line 36. FIG. 6 shows a bottom view of the implant 10 and shows how the bottom of the implant 10 is smaller than the top of the implant 10 due to inwardly tapering side walls.

Figure 7:
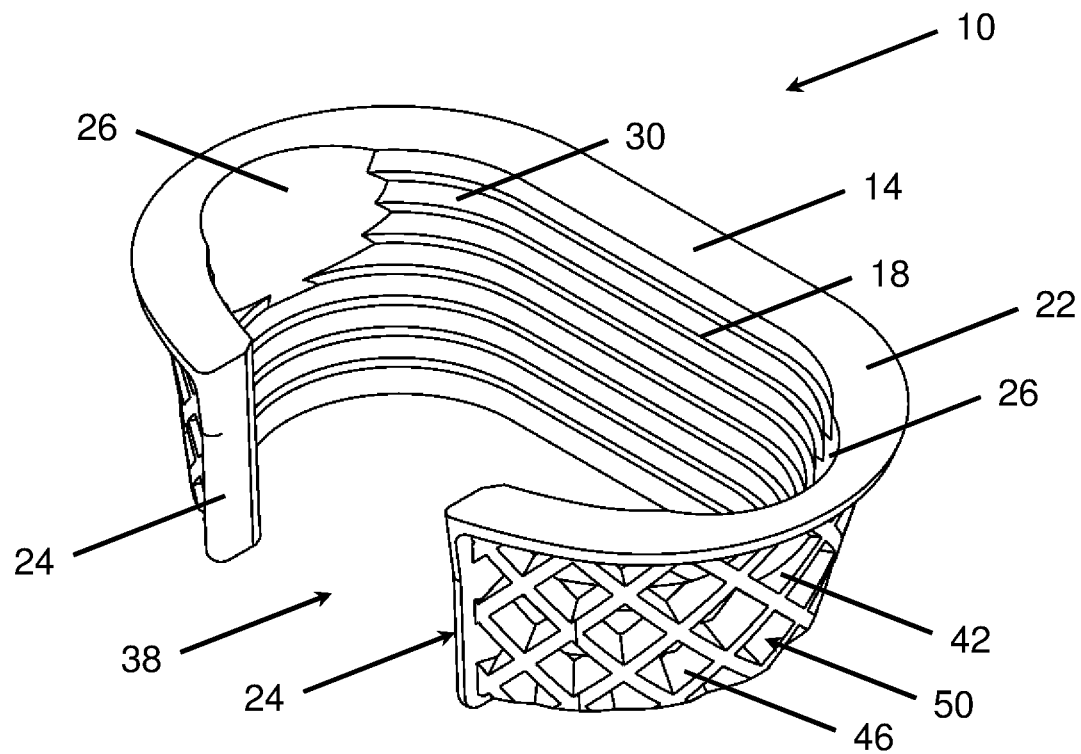
FIG. 7 is a drawing which shows the porous implant of FIG. 1.

FIG. 7 shows a perspective view of the porous implant 10 with the porous structure 34 omitted from the drawing so that the solid structure 14 is visible. The solid structure 14 defines an interior surface 18 and an upper surface 22 which are continuous and without openings. The porous implant 10 may be between about 45 mm and about 65 mm in length, between about 30 mm and about 45 mm in width, and between about 15 mm and about 20 mm in height. The interior surface 18 and upper surface 22 may often be about 1 mm thick.

The solid structure 14 includes a support structure 42 which extends outwardly from and is attached to the interior wall 18. The support structure 42 is a network of crossing walls 46 which are oriented at an angle with respect to the upper surface 22. More particularly, the support structure walls 46 are oriented at an angle of about 45 degrees relative to the top of the implant 10. Alternating support walls 46 cross each other so that the solid support structure 42 includes a grid of alternating walls 46 with square openings 50 formed between walls 46. The square openings 50 are oriented at a 45 degree angle as defined by the walls 46. In the example implant 10, the total wall thickness of the implant 10 is between about 4 mm and about 6 mm. The support walls 46 are about 1 mm thick and extend between about 2 mm and about 4 mm outwardly from the interior wall 18. The square openings 50 are approximately 6 mm in length and width and between about 2 mm and about 4 mm deep. The porous structure 34 fills the square openings 50 and also extends outwardly beyond the square openings between about 1 mm and 1.5 mm so that the porous structure 34 forms a continuous layer around the front, sides, and back of the implant 10 outside of the supporting walls 46 and openings 50 as is shown in FIG. 1.

In terms of the overall wall thickness of the implant 10, the interior wall 18 occupies about 20 percent (⅕) or about 25 percent (¼) of the wall thickness, the solid support structure 42 and the infilled porous structure 34 occupies about 50 percent (½) of the wall thickness, and the outer thickness of porous structure 34 occupies about 25 percent (¼) of the wall thickness. More generally, the interior wall thickness may be between about 5 percent (1/20) and about 35 percent (⅓) or between about 10 percent (1/10) and about 35 percent (⅓) of the implant wall thickness, the support structure 42 and infilled porous structure 34 may be between about 25 percent (¼) and about 75 percent (¾) of the wall thickness, and the layer of porous structure 34 outside of the support structure 42 may be between about 25 percent (¼) and about 50 percent (½) of the wall thickness. A porous implant 10 which provides a wall which is thicker overall may not need to substantially thicken the interior wall 18, may thicken the region with the support structure 42 and infill of porous structure 34 moderately, and may more substantially increase the thickness of the porous structure 34 outside of the support structure 42. Thus, a porous implant 10 with a wall which is about 12 mm thick may have an interior wall which is about 1 mm or about 1.5 mm thick, a support structure 42 and infill of porous structure 34 which is about 5 mm thick, and porous structure 34 outside of the support structure which is about 6 mm thick.

Figure 8:
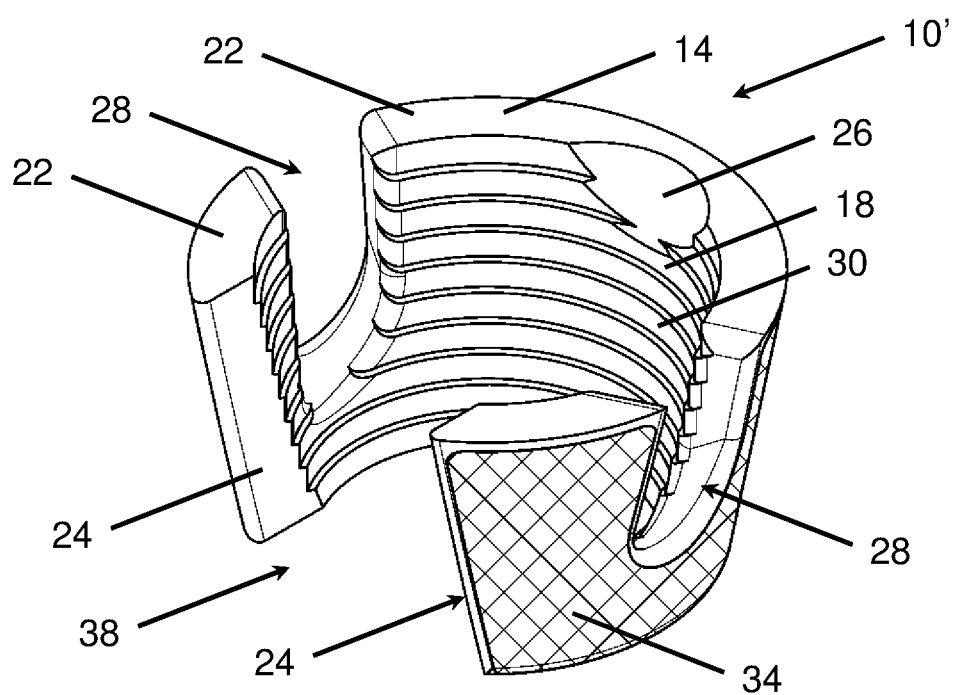
FIG. 8 is a drawing which shows a porous implant.

Turning now to FIGS. 8 through 14, another example porous implant 10' for replacing lost bone stock is shown. FIG. 8 shows a perspective view of the example porous implant 10'. Similar to the example porous implant 10 shown in FIGS. 1 through 7, this porous implant 10' is also particularly shaped for use in tibial replacement surgery or tibial joint revision surgery and is designed to fit in varying locations within the proximal epiphysis of a resected tibia. Accordingly, this porous implant 10' shares many structures with the porous implant 10 shown in FIGS. 1 through 7. Some of the structural similarities or common features between the porous implants are not explicitly discussed with respect to each example implant. These features are understood to be present in the various porous implants unless otherwise noted. The porous implant 10' fits within the proximal tibia to reinforce cancellous bone and to strengthen damaged cortical bone and thereby provide a stable supporting surface to allow a surgeon to implant an artificial tibial joint component. The porous implant 10' is designed so that the upper surface of the porous implant 10' may directly contact and support an implanted tibial component. The implant 10' is smaller in size than the implant 10 shown in FIGS. 1 through 6 and is more circular in shape. The porous implant 10' is typically between about 30 mm and about 40 mm in diameter and between about 15 mm and about 20 mm in height. The walls of the implant are typically between about 2 mm and about 5 mm in thickness The porous implant 10' includes a solid structure 14 which provides strength to the porous implant 10'. In the example implant 10', the solid structure 14 is made from laser sintered titanium powder and is solid with a somewhat rough surface resulting from the powder sintering process. The solid structure 14 forms the interior surface 18 and the upper surface 22 of the porous implant 10' as well as the inwardly facing walls 24 at the front opening 38 of the implant 10'. The implant 10' is typically installed in the end of a patient long bone so that the upper surface 22 is coplanar with a resected end of the bone. In this position, the upper surface 22 of the implant 10' may directly contact a lower facing surface of the artificial joint component to support the artificial joint component.

The porous implant 10' is generally "C" shaped when viewed from above and includes a generally rounded back wall and side walls and a front opening 38 located between the front ends of the two side walls. The round interior opening of the implant 10' is not complementary in shape to an exterior shape of an artificial joint such as an artificial tibial joint and does not directly attach to an artificial joint. That is to say that the interior opening of the porous implant 10' does not have a feature such as a Morse taper socket or another shape which is a mating fit with a corresponding portion of a lower surface of an artificial joint component and the porous implant 10' is not directly attached to an artificial joint such that it is part of the overall artificial joint. The implant 10' may be moved relative to the artificial joint component during installation of the implant 10' and is not positioned in a fixed location relative to the artificial joint component.

The interior of the implant 10' is formed with a recess 26 at the rear of the implant 10' which provides additional room for moving the implant 10' relative to an artificial joint component. The recess 26 is curved and is angled outwardly relative to the interior wall of the implant 10' and may receive a wing or flange which extends between a lower surface and a stem of a joint component to allow greater room for positioning the joint component. The porous implant 10' also includes two slots 28 which extend through the side walls of the implant 10'. The slots 28 are oriented substantially vertically although the slots are angled slightly towards the back of the implant 10' and are rotated slightly towards the back of the implant 10'. The slots 28 extend laterally through the sidewalls of the implant 10'. In the example implant 10', the slots 28 are about 6 mm wide and are about 12 mm tall. Accordingly, the height of the slots 28 is approximately two thirds of the height of the implant 10' and the width of the slots 28 is approximately one fifth of the width of the implant 10'. The interior surface 18 of the implant 10' may also include steps or ridges 30. The ridges 30 improve cement adhesion for cementing an artificial joint component such as a tibial tray to the implant 10' while installing the implant 10' and artificial joint component.

The implant 10' also includes a porous structure 34 which is illustrated in the drawings with cross hatching. In the example implant 10', the porous structure 34 is an open cell structure formed by a network of interconnected struts. The cells are typically between about 0.1 mm and about 1 mm in size and are often about 0.7 mm in size. The struts are often about 0.2 mm in diameter and may be between about 0.1 mm and about 0.8 mm in diameter. These dimensions result in a porous structure which is approximately 20 percent solid struts and about 80 percent open space. The porous structure may often be between about 10 percent solid structure and about 30 percent solid structure with a corresponding volume of open space which is between about 90 percent and about 70 percent. The porous structure 34 also forms a significant part of the porous implant 10'. In the example implant 10', the porous structure 34 forms about 65 percent of the overall implant 10' by volume. The porous structure 34 may often form between about 50 percent and about 80 percent or more of the overall implant by volume. The porous structure 34 and the solid structure 14 have a complementary shape at the interface between the solid structure 14 and the porous structure 34 so that the porous structure is joined to the solid structure without voids between the two beyond the porous structure cells. The porous structure 34 wraps around the exterior of the implant 10' so that nearly all of the exterior front, back, and sides of the implant 10' are formed by the porous structure 34. The porous structure 34 has a significantly reduced strength and stiffness as compared to the solid structure. Accordingly, the porous structure provides a strength and stiffness which is closer to that of bone and which reduces stress at the joint between the implant 10' and bone. The porous structure 34 also allows for bone ingrowth into the implant 10' to facilitate long term restoration of bone support at the prosthetic joint.

Figure 9:
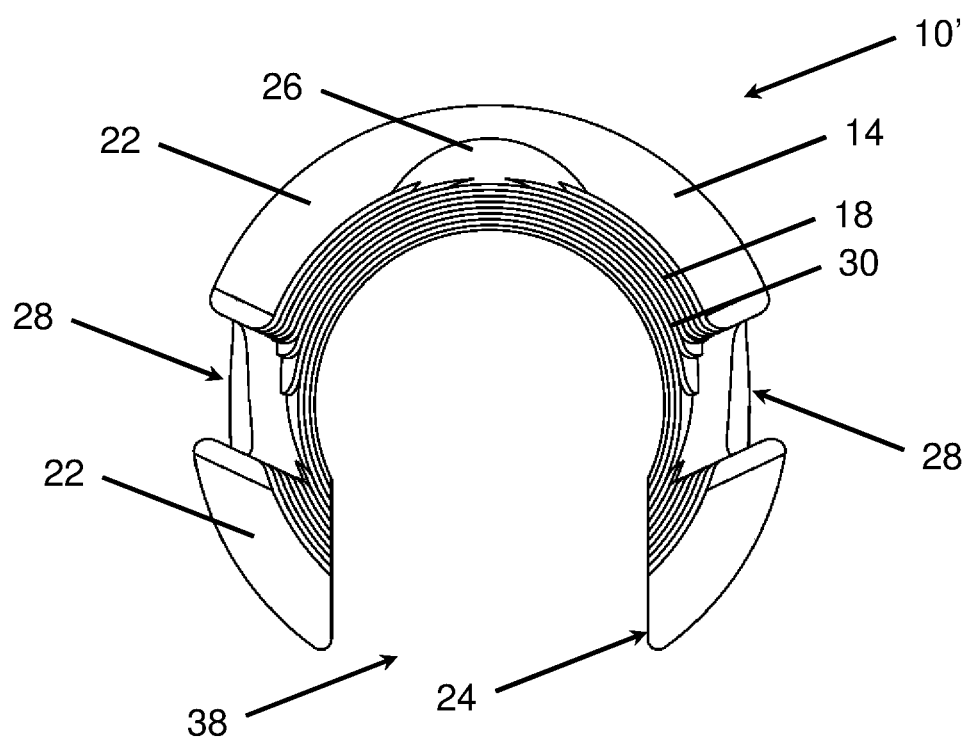
FIG. 9 is a drawing which shows the porous implant of FIG. 8.

FIG. 9 shows a top view of the implant 10'. This drawing shows the "C" shape of the implant and the opening formed at the front of the implant 10'. This drawing also illustrates the tapering shape of the implant 10'. As can be seen from the inside surface of the implant and from the other views of the implant 10', the implant tapers in size and is larger at the top than at the bottom. The implant 10' tapers in size on both the inside of the implant as well as on the outside of the implant. The inside surface 18 of the implant is roughly conical in shape (excluding features such as the slots 28 and ridges 30) and tapers inwardly. The outside shape of the implant 10' is also roughly conical in shape and tapers inwardly from the top to the bottom of the implant 10'. The inside and outside surfaces of the implant 10' may taper inwardly by an angle which is between about 10 and about 15 degrees. The front opening 38 is vertical when viewed from the front and the front ends 24 of the side walls are vertical when viewed from the front.

Figure 10:
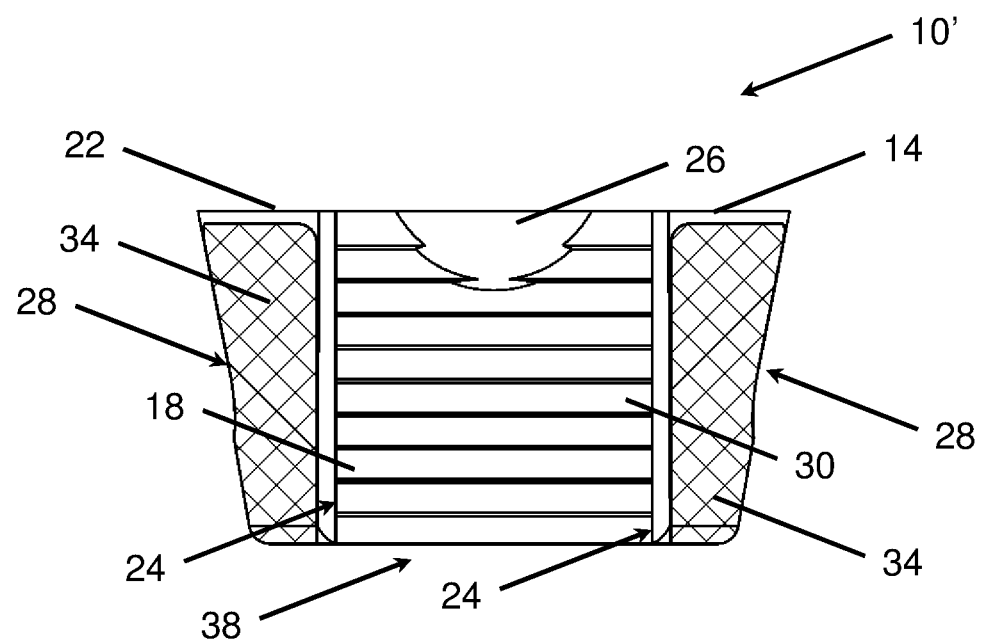
FIG. 10 is a drawing which shows the porous implant of FIG. 8.
Figure 11:
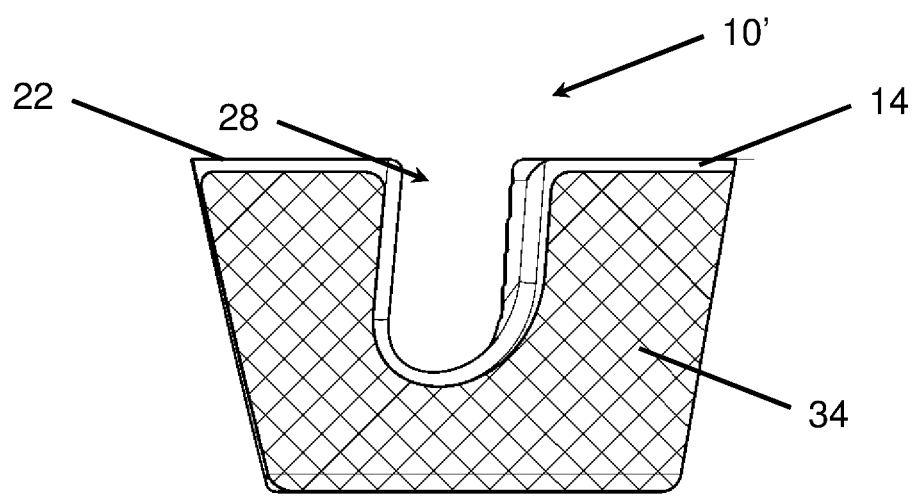
FIG. 11 is a drawing which shows the porous implant of FIG. 8.
Figure 12:
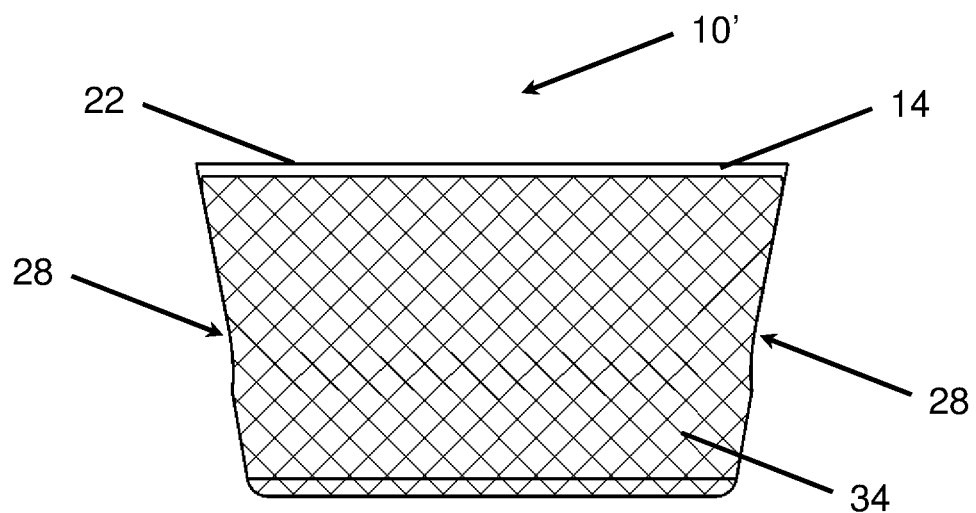
FIG. 12 is a drawing which shows the porous implant of FIG. 8.
Figure 13:
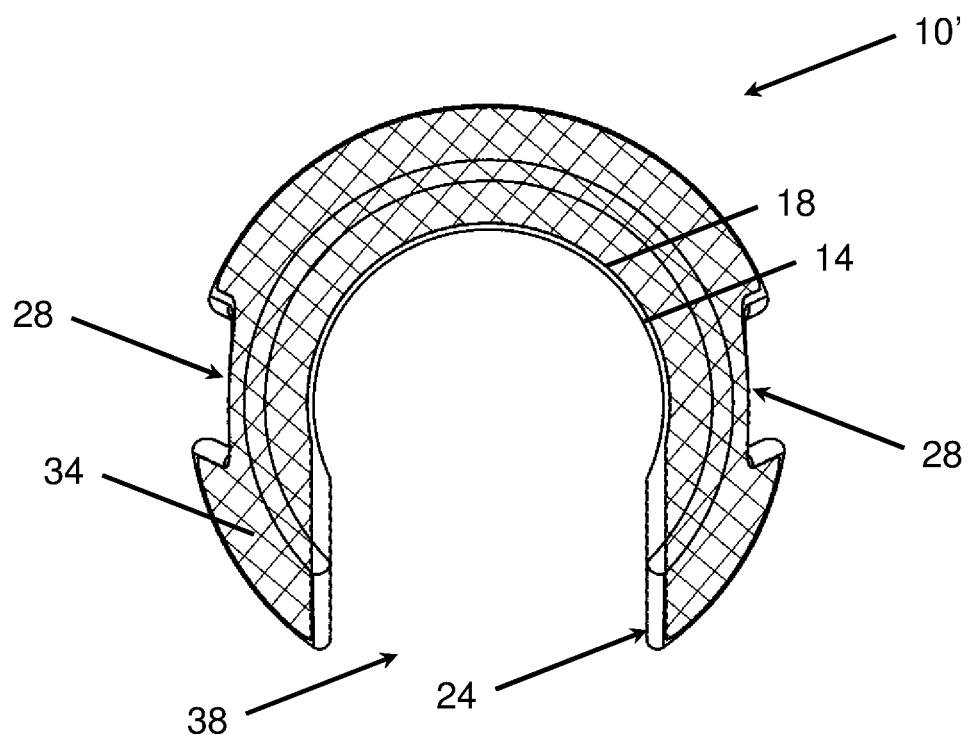
FIG. 13 is a drawing which shows the porous implant of FIG. 8.

FIG. 10 shows a front view of the implant 10', illustrating how the sides of the implant 10' taper inwardly. FIG. 11 shows a side view of the porous implant 10' and also shows how the back of the implant 10' tapers inwardly. The opposite side of the implant 10' is symmetrical to the side shown. FIG. 12 shows a back view of the implant 10' and shows how the sides of the implant taper inwardly. It can also be seen how the porous structure 34 extends across the back of the implant 10'. FIG. 13 shows a bottom view of the porous implant 10' and illustrates how the bottom is smaller than the top of the implant 10'.

Figure 14:
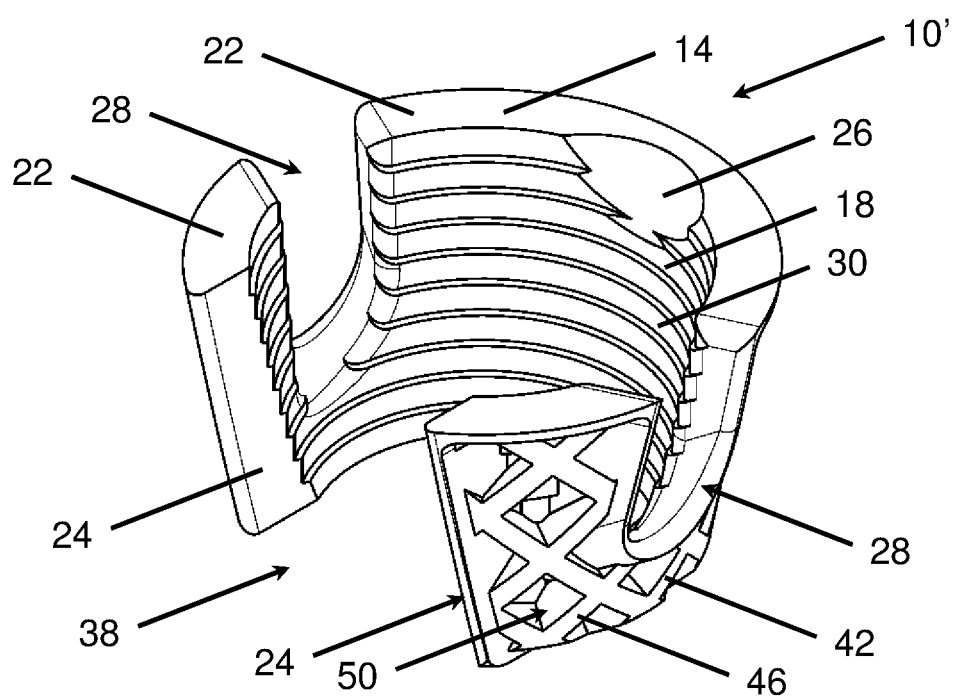
FIG. 14 is a drawing which shows the porous implant of FIG. 8.

FIG. 14 shows a perspective view of the porous implant 10' with the porous structure 34 omitted from the drawing so that the solid structure 14 is visible. The solid structure 14 defines an interior surface 18 and an upper surface 22 which are continuous and without openings. The solid structure 14 includes a support structure 42 which extends outwardly from and is attached to the interior wall 18. The support structure 42 is a network of crossing walls 46 which are oriented at an angle with respect to the upper surface 22. More particularly, the support structure walls 46 are oriented at about 45 degrees relative to the top or bottom of the implant 10 and alternating walls 46 cross each other so that the solid support structure 42 includes a grid of alternating walls 46 with square openings 50 formed between walls. The square openings 50 are oriented at a 45 degree angle as defined by the walls 46. In the example implant 10, the total wall thickness of the implant 10 is about 5 mm. The support walls 46 are about 1 mm thick and extend about 2 mm outwardly from the interior wall 18. The square openings 50 are approximately 6 mm in length and width and about 2 mm deep. The porous structure 34 fills the square openings 50 and also extends outwardly beyond the square openings approximately 1.5 mm so that the porous structure 34 forms a continuous layer around the front, sides, and back of the implant 10 outside of the supporting walls 46 and openings 50 as is shown in FIG. 8.

Figure 15:
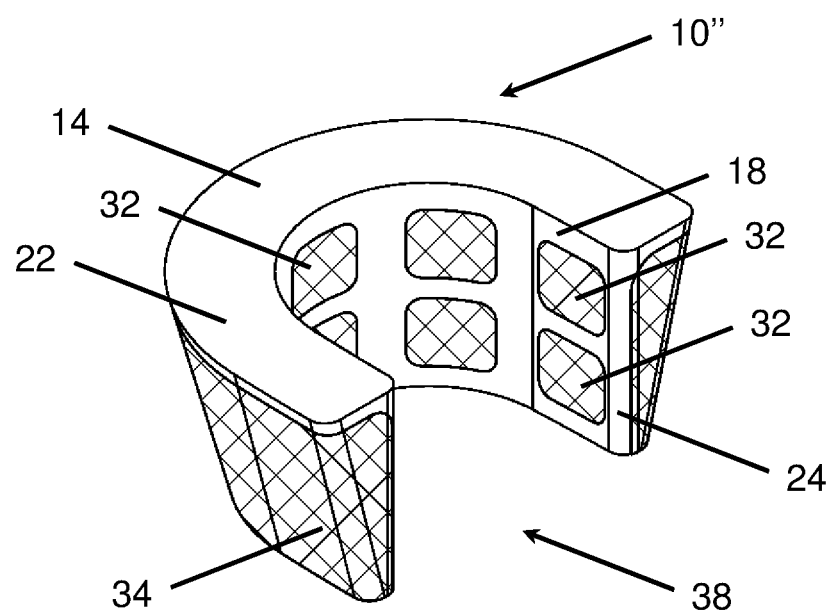
FIG. 15 is a drawing which shows a porous implant.

Turning now to FIGS. 15 through 20, another example porous implant 10" for replacing lost bone stock is shown. FIG. 15 shows a perspective view of the example porous implant 10". Similar to the example porous implants 10 and 10' shown in FIGS. 1 through 14, this example porous implant 10" is also particularly shaped for use in tibial replacement surgery or tibial joint revision surgery and is primarily designed to fit in varying locations within the proximal epiphysis of a resected tibia. Accordingly, this porous implant 10" shares many structures with the porous implants 10 and 10' shown in FIGS. 1 through 14. The porous implant 10" fits within the proximal tibia to reinforce cancellous bone and to strengthen damaged cortical bone and thereby provide a stable supporting surface to allow a surgeon to implant an artificial tibial joint component. The porous implant 10" is designed so that the upper surface of the porous implant 10" may directly contact and support an implanted tibial component. The implant 10" has a circular rear portion with side walls extending from the rear portion. The porous implant 10" is typically between about 30 mm and about 35 mm wide, between about 20 mm and about 25 mm long front to back, and about 15 mm in height. The walls of the implant are typically between about 3 mm and about 5 mm in thickness The porous implant 10" includes a solid structure 14 which provides strength to the porous implant 10". In the example implant 10", the solid structure 14 is made from laser sintered titanium powder and is solid with a somewhat rough surface resulting from the powder sintering process. The solid structure 14 forms the interior surface 18 and the upper surface 22 of the porous implant 10". The implant 10" is typically installed in the end of a patient long bone so that the upper surface 22 is coplanar with a resected end of the bone. In this position, the upper surface 22 of the implant 10" may directly contact a lower facing surface of the artificial joint component to support the artificial joint component.

The porous implant 10" is generally "C" shaped when viewed from above and includes a generally round back wall and straight sides and a front opening 38 located between the two sides. The round interior opening of the implant 10" is not complementary in shape to an exterior shape of an artificial joint such as an artificial tibial joint and does not directly attach to an artificial joint. That is to say that the interior opening of the porous implant 10" does not have a feature such as a Morse taper socket or another shape which is a mating fit with a corresponding portion of a lower surface of an artificial joint component and the porous implant 10" is not directly attached to an artificial joint such that it is part of the overall artificial joint. The implant 10" may be moved relative to the artificial joint component during installation of the implant 10" and is not positioned in a fixed location relative to the artificial joint component.

The exterior side walls of the implant 10" are at an angle of about 75 degrees relative to horizontal and thus taper inwardly at an angle of about 15 degrees relative to vertical. The interior surface 18 of the implant 10" has generally vertical walls and does not taper inwardly as the outer walls do. The interior surface 18 of the implant 10" may include bonding sections 32 of increased roughness which improve cement adhesion for cementing an artificial joint component such as a tibial tray to the implant 10" while installing the implant 10" and artificial joint component. The bonding sections 32 may be sections which are sintered to increase the surface roughness, such as by providing an irregular surface edge or small projections. The bonding sections 32 may also be sections of porous structure which is similar to the external porous structure 34.

The implant 10" also includes a porous structure 34 which is illustrated in the drawings with cross hatching. In the example implant 10", the porous structure 34 is an open cell structure formed by a network of interconnected struts. The cells are typically between about 0.7 mm and about 2 mm in size and are often about 1 mm in size. The struts are often about 0.2 mm in diameter and may be between about 0.1 mm and about 0.8 mm in diameter. These dimensions result in a porous structure which is approximately 20 percent solid struts and about 80 percent open space. The porous structure may often be between about 10 percent solid structure and about 30 percent solid structure with a corresponding volume of open space which is between about 90 percent and about 70 percent. The porous structure 34 also forms a significant part of the porous implant 10". In the example implant 10", the porous structure 34 forms about 65 percent of the overall implant 10" by volume. The porous structure 34 may often form between about 50 percent and about 80 percent or more of the overall implant by volume. The porous structure 34 and the solid structure 14 have a complementary shape at the interface between the solid structure 14 and the porous structure 34 so that the porous structure is joined to the solid structure without voids between the two. The porous structure 34 wraps around the exterior of the implant 10" so that nearly all of the exterior front, back, and sides of the implant 10" are formed by the porous structure 34. The porous structure 34 has a significantly reduced strength and stiffness as compared to the solid structure. Accordingly, the porous structure provides a strength and stiffness which is closer to that of bone and which reduces stress at the joint between the implant 10" and bone. The porous structure 34 also allows for bone ingrowth into the implant 10" and can facilitate long term restoration of bone support at the prosthetic joint.

Figure 16:
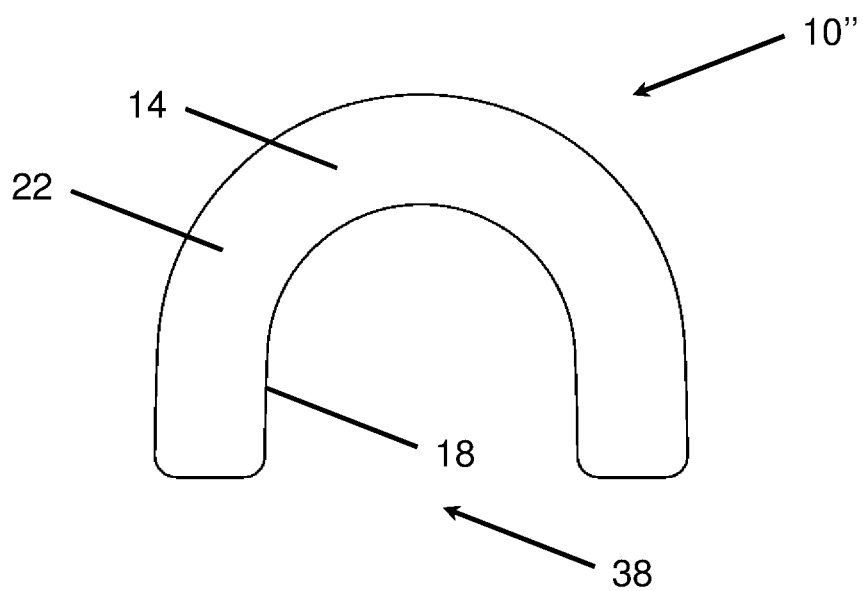
FIG. 16 is a drawing which shows the porous implant of FIG. 15.
Figure 17:
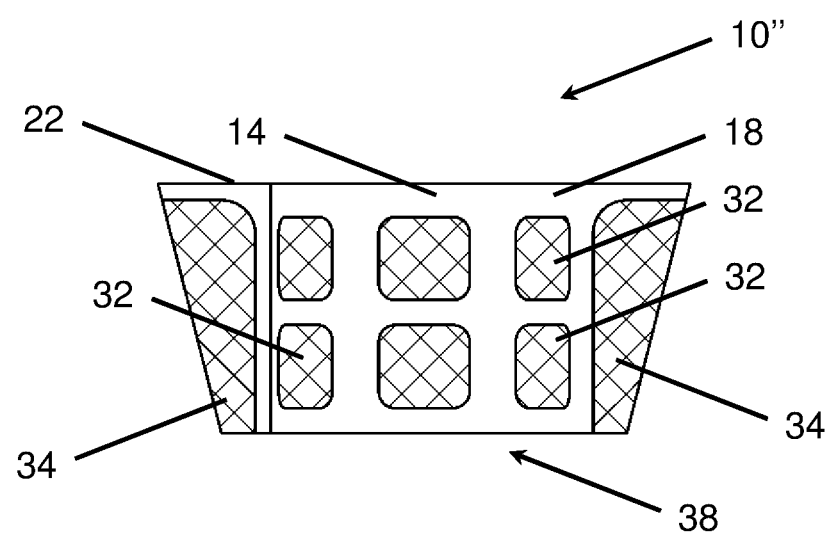
FIG. 17 is a drawing which shows the porous implant of FIG. 15.
Figure 18:
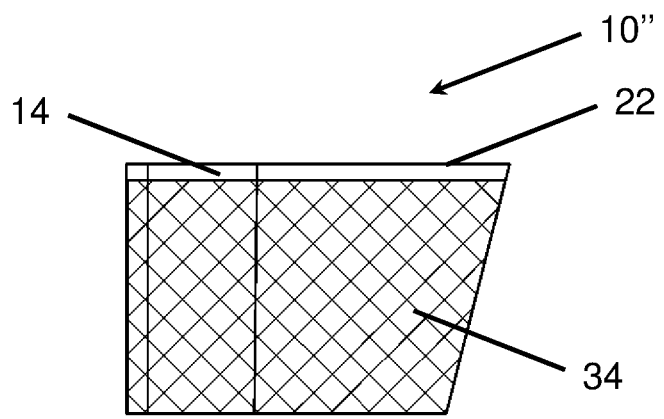
FIG. 18 is a drawing which shows the porous implant of FIG. 15.
Figure 19:
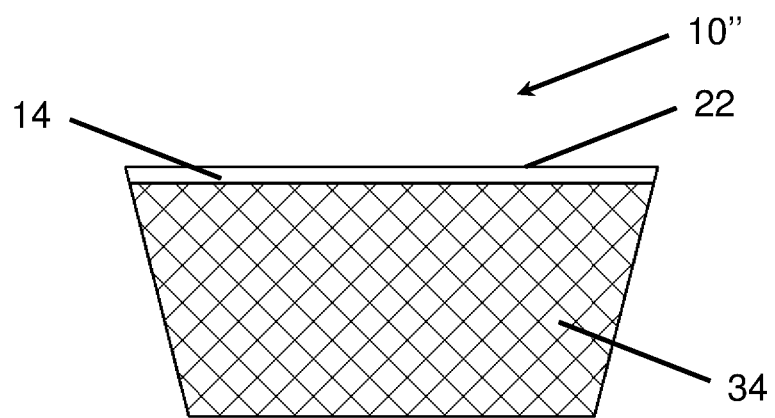
FIG. 19 is a drawing which shows the porous implant of FIG. 15.
Figure 20:
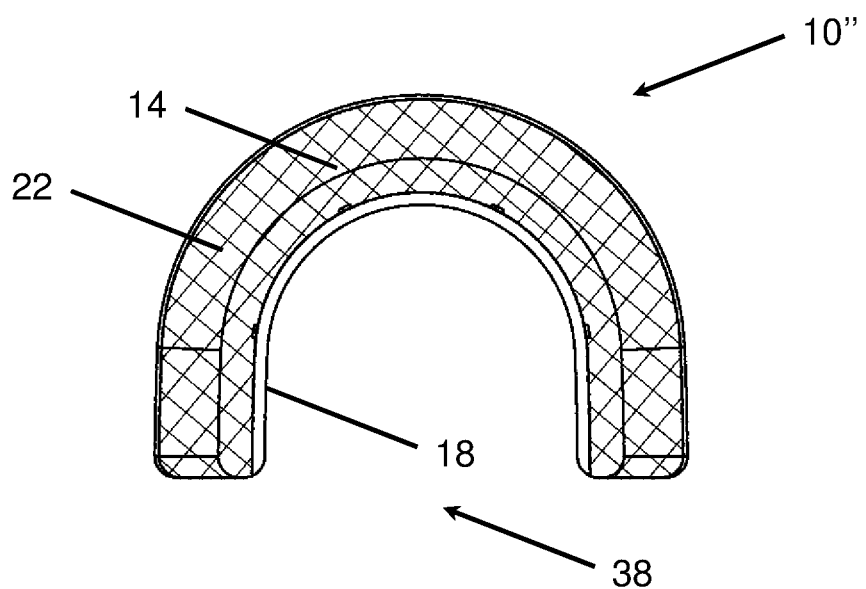
FIG. 20 is a drawing which shows the porous implant of FIG. 15.

FIG. 16 shows a top view of the implant 10". This drawing shows the "C" shape of the implant and the opening 38 formed at the front of the implant 10". The front opening 38 is vertical when viewed from the front and the front ends 24 of the side walls are vertical when viewed from the front. FIG. 17 shows a front view of the implant 10", illustrating how the sides of the implant 10" taper inwardly. FIG. 18 shows a side view of the porous implant 10" and also shows how the back of the implant 10" tapers inwardly. FIG. 19 shows a back view of the implant 10" and shows how the sides of the implant taper inwardly. It can also be seen how the porous structure 34 extends across the back of the implant 10". FIG. 20 shows a bottom view of the implant 10" and illustrates how the bottom is smaller than the top of the implant 10".

Figure 21:
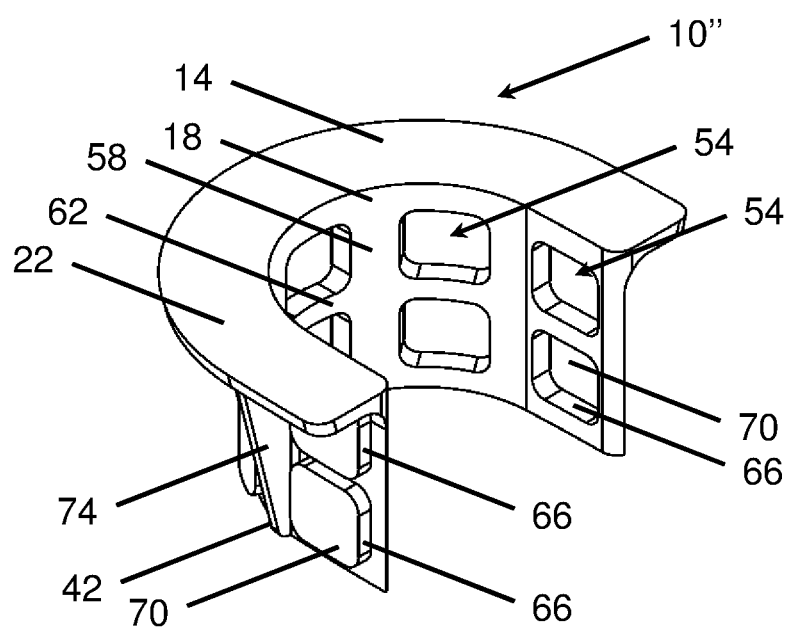
FIG. 21 is a drawing which shows the porous implant of FIG. 15.

FIG. 21 shows a perspective view of the porous implant 10" with the porous structure 34 omitted from the drawing so that the solid structure 14 is visible. The solid structure 14 defines an interior surface 18 and an upper surface 22. The solid structure 14 includes a support structure 42 which extends outwardly from the interior (vertical) wall 18 and is attached to the interior wall 18. In the example implant 10", the solid structure 14 includes recesses 54 formed therein. The recesses 54 form openings which pass through the interior wall 18 and interrupt the interior wall 18. The recesses/openings 54 are disposed in an array around the interior wall 18 with two rows of five recesses/openings 54. The interior wall 18 is separated into a series of vertical supports 58 and horizontal braces 62 extending between the vertical supports. The recesses 54 include flanges 66 which extend outwardly from the interior wall 18 around the perimeter of the openings 54. In the example implant 10", the flanges 66 extend outwardly from the inside wall by a distance of about 1.5 mm and extend around the entire perimeter of the openings 54. A recess closure wall 70 spans across the outside end of each of the flanges 66 to close the opening 54. Accordingly, each opening 54, flange 66, and closure wall 70 forms a closed recess or pocket in the inside wall 18. In the area of each recess 54, the closure wall 70 is generally parallel to the inside wall 18 but is displaced away from the inside of the implant 10".

Figure 22:
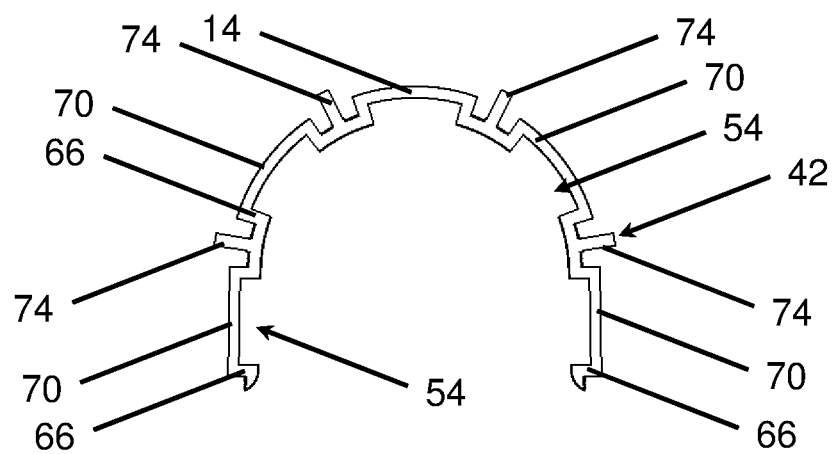
FIG. 22 is a drawing which shows the porous implant of FIG. 15.

FIG. 22 shows a cross section of the solid structure 14 of the implant 10" taken through the upper row of openings 54 and better illustrates the shape of the opening 54, flange 66, and closure wall 70. The flange 66 extends outwardly from the interior wall 18 about 1.5 mm and creates a pocket 54 which is about 1 mm or about 1.5 mm deep. The closure wall 70 is displaced from the inside wall by about 1.5 mm and the closure wall 70 is located outside of the plane of the interior wall 18. The closure wall is typically about 1 mm thick. This creates a jog is the interior wall 18 so that the interior wall 18 does not follow a smooth line/curve in a horizontal plane. The support structure 42 also includes vertical walls 74 which extend upwardly from the bottom of the interior wall 18 to the top of the interior wall 18 and along the bottom of the top surface 22. Four vertical walls 74 are located between the openings 54. As the walls of the implant 10" taper from top to bottom, the vertical support walls 74 also taper from top to bottom. The vertical walls 74 are wider at the top and support the underside of the top surface 22 and are narrow at the bottom.

In the example implant 10", the total wall thickness of the implant 10" is between about 3 mm and about 5 mm. The wall of the implant is about 5 mm wide at the top of the implant 10" and tapers to about 3 mm thick at the bottom of the implant. The vertical support walls 74 are about 1 mm thick and extend about 3 mm outwardly from the interior wall 18 at the top of the implant and about 1 mm from the interior wall at the bottom of the implant. The openings 54 are approximately 5 mm in length and width and about 1.5 mm deep. The porous structure 34 fills the openings/recesses 54 on the inside of the implant 10. The porous structure 54 also fills around the exterior of the solid structure 14 and extends outwardly beyond the closure walls 70 and vertical support walls 74 by approximately 1 mm so that the porous structure 34 forms a continuous layer around the front, sides, and back of the implant 10" as is shown in FIG. 15.

Figure 23:
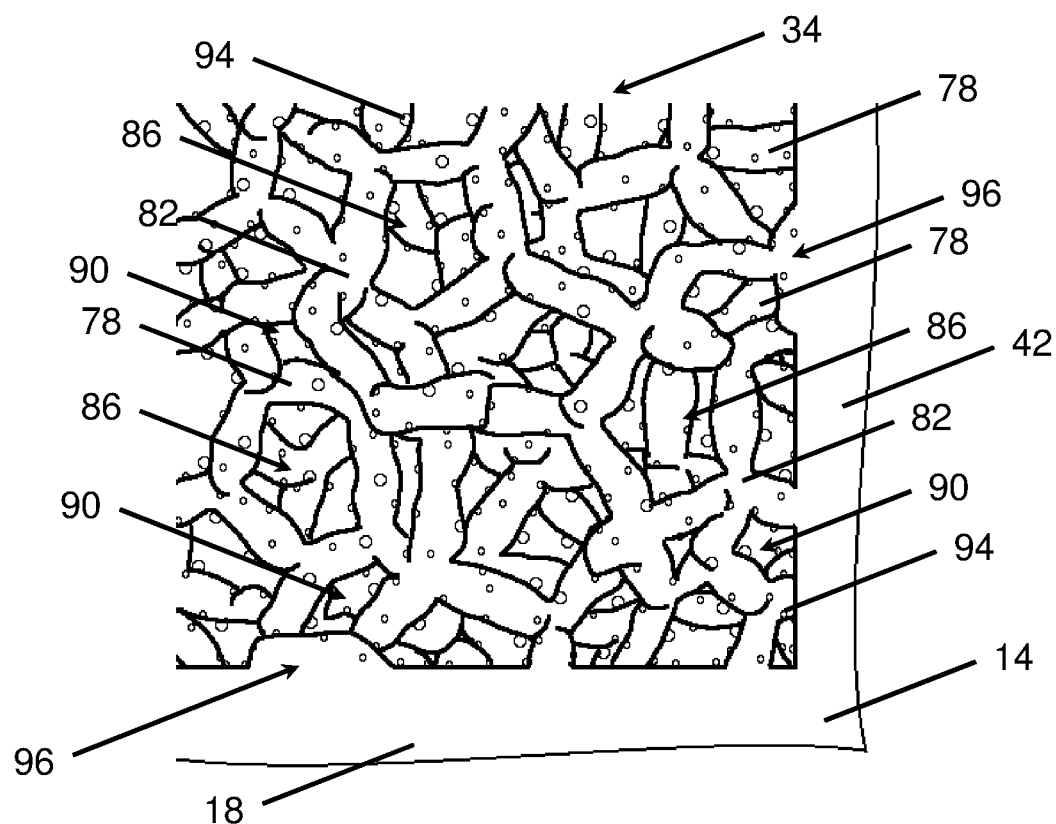
FIG. 23 is a drawing which shows the porous structure.

FIG. 23 shows a drawing of the porous structure 34. As discussed, the porous structure 34 is manufactured by laser sintering of titanium powder. The laser sintering process used by Applicants provides unique properties to the finished strut including shape and surface characteristics. The example porous structure 34 includes a large number of struts 78 which are fused together at nodes 82. Generally, the struts 78 are aligned along edges of polyhedral geometric shapes with the nodes 82 positioned at the vertices. The structure of the struts 78 forms a number of open cells 86 with windows 90 between adjacent cells 86. In one example, the cells 86 may approximate 12 or 14 sided polyhedral cells and any given cell may have 6 or more windows 90 to adjacent cells 86. In the example porous structure, the struts 78 are approximately 0.2 mm in diameter and are approximately 0.5 mm in length. The example porous structure includes nodes 82 which are generally not enlarged beyond simply joining adjacent struts. The cells 86 located between struts are between approximately 0.7 mm and 1 mm in size and may often have an irregular oval shape. The windows 90 between adjacent cells are often between about 0.3 mm and about 0.5 mm in size.

Struts 78 which may be uniform in a theoretical model become irregular in shape and diameter when laser sintered from titanium powder. The layer by layer sintering of a strut 78 which extends through several sintering layers results in a strut 78 which has several bulbous sections connected by somewhat thinner sections. This irregularity in size and shape of the struts 78 can be seen. It can also be seen how the struts 78 become covered by small nodules 94 of titanium. The struts 78 are covered with varying sizes of bumps or nodules 94 of titanium. When the porous implant is laser sintered, a volume of titanium powder is melted by the laser to form the strut 78. Particles of titanium which are largely within the strut volume but which are partially outside of the strut volume may melt into the strut and form a bulge or protuberance on the strut 78. Particles of titanium powder adjacent the volume of the sintered strut 78 may stick to the strut when the strut 78 is sintered.

This results in the rough and irregular surface shown in FIG. 23. The surface of the porous implant, including both struts 78 and nodes 82 in the porous structure 34 and surfaces of the solid structure 14 have varying sizes of titanium nodules 94 randomly distributed across the surface. The titanium nodules 94 are often similar in size to the titanium powder used to form the porous implant. The surface nodules 94 provide an amount of surface roughness which is beneficial for bone ingrowth and cement adhesion. Manufacture of the porous implant by laser sintering of titanium powder thus provides a unique surface which is naturally irregular and rough and suitable for bone and cement adhesion.

FIG. 23 also shows how the porous implant 10 may be manufactured as a single monolithic structure including both the solid structure 14 and the porous structure 34 via additive manufacturing such as direct metal laser sintering. FIG. 23 shows a portion of the interior wall 18 and the reinforcing structure 42, such as a wall 46 or 74. By laser sintering the porous implant 10, the solid structure 14 is integrally formed with the porous structure 34 and these are joined together where struts 78 intersect the solid structure 14 as indicated at locations 96. This reduces manufacturing costs by eliminating additional bonding steps and increases the strength and reliability of the porous implant 10. Other materials can be used to manufacture the porous implant through laser sintering as discussed herein. Metal powder such as cobalt chrome metals or stainless steel or ceramic powder could also be laser sintered as discussed herein to manufacture the porous implant.

Figure 24:
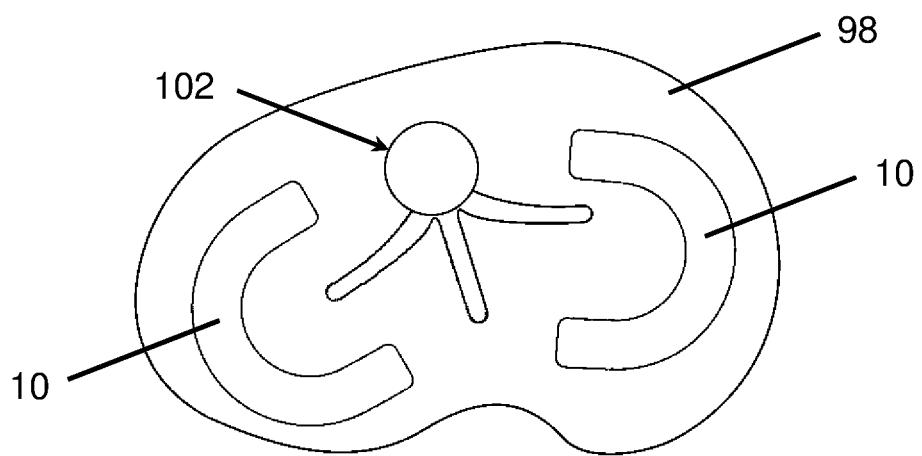
FIG. 24 is a drawing showing an example use of a porous implant.

FIG. 24 shows a drawing which illustrates an example use of the porous implants 10 (which may be any of implants 10, implants 10', and implants 10"). Two small porous implants 10 have been used to repair bone stock in a tibia 98. The proximal end of a tibia 98 has been resected to receive a tibial component of an artificial knee joint. In performing the resection, the surgeon identified areas within the tibia 98 which provided insufficient support for the tibial joint component. Porous implants 10 were installed into the tibia 98 in order to repair the bone and provide support for the tibial joint component. The porous implant 10 may be installed after removal of bone if necessary. The approximate location where a tibial implant with a stem and keel would be installed into the bone 98 is indicated at 102. As indicated, the porous implant 10 is not limited to a fixed position relative to the joint component and is not attached to the joint component by a mating feature such as a Morse taper joint. The upper surfaces of the porous implants 10 will typically contact and support the lower surface of the joint component.

Figure 25:
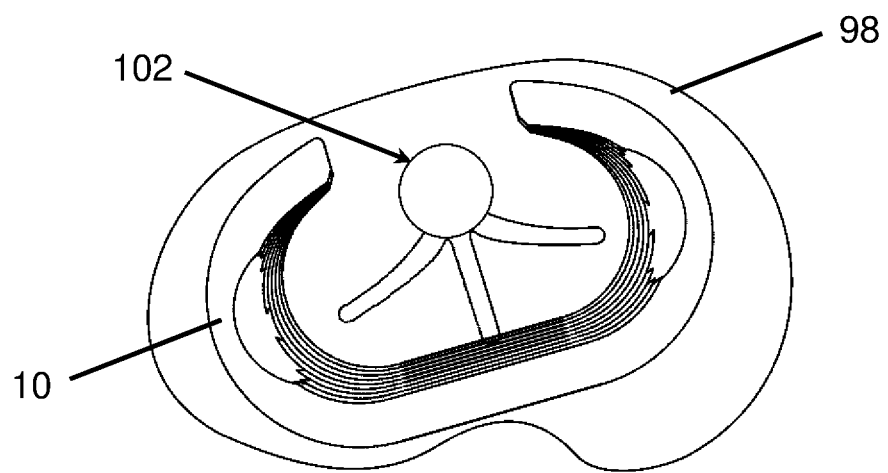
FIG. 25 is a drawing showing an example use of a porous implant.

FIG. 25 shows a drawing which illustrates another example use of the porous implants 10. A large porous implant 10 has been used to repair bone stock in a tibia 98. The proximal end of a tibia 98 has been resected to receive a tibial component of an artificial knee joint and a large porous implant 10 was installed into the tibia 98 in order to repair the bone and provide support for the tibial joint component. The approximate location where a tibial implant with a stem and keel would be installed into the bone 98 is indicated at 102. As indicated, the porous implant 10 is not limited to a fixed position relative to the joint component and is not attached to the joint component by a mating feature such as a Morse taper joint.

FIG. 26 shows a drawing which illustrates another example use of the porous implants 10. A small porous implant 10 has been used to repair bone stock in a femur 106. The distal end of a femur 106 has been resected to receive a femoral component of an artificial knee joint and a small porous implant 10 was installed into the femur where a bone defect 110 was present in order to repair the bone and provide support for the femoral joint component. As indicated, the porous implant 10 is not limited to a fixed position relative to the joint component and is not attached to the joint component by a mating feature such as a Morse taper joint. The porous implant 10 may be used in various different situations to remedy bone defects particularly during the installation of a primary or revision prosthetic joint.

The "C" shaped structure of the porous implants 10 is advantageous in treating the types of bone defects that are commonly encountered while installing artificial joints. The porous implants 10 are not keyed to a prosthetic joint or held in a fixed position relative to the prosthetic joint; they may be moved to different locations within the bone. The porous implants 10 may be positioned where they best address the bone damage and where they best provide support for a prosthetic joint. The "C" shape of the porous implants 10 and the front opening 38 allows the implants to be placed in varying locations around the perimeter of a bone where they can interface with cortical and cancellous bone to strengthen the bone and support a prosthetic joint. The "C" shape of the porous implant allows the porous implant to fill common peripheral defects in the bone without interfering with the installation of a prosthetic joint component afterwards. As is shown in FIGS. 21 through 23, the porous implants 10 may be installed into the bone in many different locations and may be oriented to allow the stems or wings which are present on many prosthetic joints to extend through the front opening and into the center of the porous implant. This allows the porous implants 10 to repair bone defects in locations which overlap with locations occupied by the prosthetic joint as well as in locations surrounding a prosthetic joint. The porous implant 10 may be positioned in the location which best repairs the bone defect and may be oriented such that the front opening 38 and the open center of the "C" shape may receive a stem or wing present on the prosthetic joint in the area of the porous implant. The porous implants 10 may be used in combination with many different brands and styles of prosthetic joint components.

The porous implants may be advantageously fabricated by additive manufacturing such as by laser sintering a porous implant from titanium powder using the Direct Metal Laser Sintering process. Laser sintering the device from titanium powder significantly reduces the cost of producing the device as compared to other methods of manufacturing a porous metal foam. A laser sintering machine will sinter a thin layer of metal powder to fuse the metal particles together and to a previously sintered layer in a desired geometry. Multiple thin layers are sintered together to form the finished part. The laser sintering machine typically places a build plate in a rectangular enclosure which may be filled with powder and which has an open top exposed to the laser sintering beam. A laser or other energy beam is directed towards the powder by a focusing head mounted to a gantry, a movable mirror, or other CNC mechanism in order to selectively aim and fire the laser to selectively sinter the top layer of metal powder into the desired part. The build plate is moved downwardly in the enclosure a distance equal to the layer height after sintering each layer and metal powder is added above the build plate for sintering the next layer. The laser then sinters the metal powder for the next incremental Z height of the part. The process is repeated until the entire part has been sintered.

Laser sintering does, however, have its own limitations. Because the parts are sintered layer by layer, stresses build up in the resulting construct. Internal stresses develop in laser sintered parts because the sintered layers contract as they solidify and cool. Subsequently sintered layers are sintered onto and attached to already solidified and partially cooled layers and contract as they then solidify and cool; causing the subsequent layer to shrink relative to previous layers. The part wants to curl upwardly due to the internal stresses.

Applicants discovered that parts which are entirely made from a highly porous open celled structure generally do not accumulate unmanageable internal stress while sintering. A porous structure which is comprised of thin struts joined at small nodes to define open cells framed between struts with windows or openings between cells is relatively flexible and the shape of the structure does not generate significant internal stress while sintering. Entirely porous parts, however, lacked strength in areas such as where the porous implant 10 contacts and supports the tibial component. Parts which are made entirely or largely from solid structure can be undesirable for bone replacement implants because the part is significantly stronger than the bone and can cause stress risers and stress shielding of the bone.

In order to create a porous implant with sufficient strength, Applicants added a solid interior (vertical) wall 14 and a solid upper support surface 22. Applicants identified problems making porous parts with a solid interior wall and upper surface. The addition of these solid structures created problems with warping and cracking. In making the porous implants, Applicants discovered that the structure was particularly susceptible to internal stress buildup from sintering. The stress in the implants were sufficient to cause warping or cracking in the construct. In some instances, the porous implant would warp and pop off of the build plate while sintering the porous implant. Applicants understand that part of this may be due to the fact that the porous implants as a whole are relatively thin walled and are an open "C" shape with side walls, a back wall, and a front opening. If the solid interior wall and upper support surface were thick enough to provide a desired strength to the implant, the part experienced warping problems. If the solid interior wall and upper support surface were sufficiently thin to not cause warping problems, they were not sufficiently thick to provide the desired amount of strength to the implant.

The warping and cracking problems were then remedied by including a support structure 42 as part of the solid structure of the porous implant. The support structure is designed to provide additional strength to the solid structure without also contributing to the internal stress from sintering the solid structure. The support structure is also designed to mitigate internal stresses in the solid structure. The support structure includes walls and structures which are oriented out of plane and out of alignment with the solid structure walls. Support structure features are oriented at an angle relative to the plane normal to the Z axis (the sintering plane). The support structure features are oriented at an angle between about 20 degrees and about 90 degrees relative to the sintering plane (i.e. at an angle greater than about 20 degrees relative to the sintering plane). Preferably, the support structure features are oriented at an angle between about 30 degrees and about 90 degrees relative to the sintering plane. Support walls 46 are preferably oriented at an angle of about 45 degrees to the sintering plane. Support walls 74 are oriented at an angle of about 90 degrees to the sintering plane. Pocket closure walls 70 are oriented at an angle of about 90 degrees relative to the sintering plane. This geometry results in these support features being separated into many different sintering layers without significant continuous structures in any particular sintering layer where the implant is sintered layer by layer using the additive manufacturing process. This minimizes the internal stress generated within the support structure features.

The support structure features are also oriented to help offset the internal stresses generated from sintering the solid structure interior wall 18 and upper support surface 22. In creating the porous implant 10, the solid structures are oriented to minimize their overall internal stresses. The curved internal wall 18 tends to pull inwardly due to the internal stresses from sintering. Support structure walls 46, 74 located outside of the internal wall 18 tend to pull outwardly on the internal wall 18 due to the internal stress (tension) from sintering. In this manner, the support structure walls 46, 74 stabilize the interior wall 18.

The pockets 54 with the outward flanges 66 and closure walls 70 interrupt the interior wall 18 and provide bends along the sintering plane. The pocket closure walls 70 are displaced sufficiently that they are misaligned with the interior wall 18. This design breaks up the tension present in the interior wall 18 from sintering and provides bends where the interior wall 18 can flex and relieve tension from sintering.

The support structure 42 mitigates interior stress from sintering sufficiently to eliminate problems with warping or cracking in the porous implant. Stress analysis of the porous implants 10 without the support structure 42 shows a high degree of tensile stress is in the interior wall 18. It is this stress that causes warping and cracking in the implant. Stress analysis of the porous implants 10 with the support structure 42 shows little tensile stress in the interior wall 18 and shows a moderate degree of tensile stress in the outer surfaces of the support structure 42. The overall stress in the porous implant is significantly reduced and the stress is isolated to smaller segments of the porous implant instead of being present across large continuous surfaces. The reinforcing structure allows a significantly thinner interior wall to be used while achieving the desired strength in the porous implant.

The porous implant can be manufactured in a single monolithic structure including the solid structure, the porous structure, and surface roughness. The solid structure and the porous structure are manufactured together as each layer of the porous implant is sintered together by additive manufacturing. Accordingly, the porous structure and the solid structure are completely bonded to each other and possible failure points between the porous structure and the solid structure are avoided. The surface roughness is formed during manufacture of the porous implant and further processing to add additional material such as a porous bead coating is unnecessary. These features make the porous implant reliable and economical.

As discussed herein, "solid structure" or "solid" refers to a structure within the porous implant which is manufactured to form a substantially solid material. It is understood that this solid material may contain micro porosity, surface roughness, etc., but is otherwise solid or substantially solid material within the shape of the structure. In contrast, "porous structure" as used herein refers to an overall structure which is highly porous even though formed of structures of a solid material. The porous structure is often formed as an open celled structure which includes a network of struts and nodes (joints between struts) with open cells as well as open windows between adjacent cells defined by the struts and nodes. The struts and nodes are formed from solid material but the overall porous structure incorporates a large amount of void space in its cells and pores.

Thus, the porous implants include a large volume of highly porous structure 34 coupled to a solid structure 14 including an internal wall 18, an upper support surface 22, and a support structure 42. The solid structures 14 provide adequate support where the porous implant 10 supports an artificial joint such as a tibial artificial joint component. The adjacent porous structure provides a significantly reduced modulus material which is more compatible with the properties of the bone to which it is attached. The support structure 42 manages internal stresses within the solid structure 14 from the sintering process in a way that prevents the overall porous implant from warping or cracking and allows the porous implant to be made successfully by powder bed fusion techniques such as laser sintering.

The porous implants 10 and 10' include internal walls 18 which are solid or largely solid and upper surfaces 22 which are solid or largely solid in order to support the prosthetic joint component. Simply having the interior wall 18 and upper surface 22 made of solid sintered titanium, however, results in warping or cracking problems. The diagonally crossing walls 46 of the support structure 42 prevent the warping and cracking problems in the porous implant 10, 10'. The diagonally crossing walls 46 add torsional rigidity and bending stiffness to the porous implant. The diagonal support walls 46 are oriented on the solid structure 14 so that they have minimal size on any particular layer. The diagonal support walls 46 do not add significant internal stresses to the porous implant because they do not have significant continuous horizontal sections in any particular layer of the construct. In each layer of the porous implant, the diagonal support walls 46 are a small strut extending outwardly from the interior wall 18. This portion of the support wall 46 is short and narrow and has minimal internal stresses as it cools. Because it is not continuous and not aligned with the interior wall 18, it contributes little to the internal stress of the overall construct while bracing the interior wall against warping.

The porous implant 10" is also strengthened against warping or cracking by its support structure 42. The recesses 54 formed by openings in the interior wall 18, flanges 66 extending outwardly around the perimeter of the opening, and closing walls 70 mitigate sintering stresses within the interior wall 18. In sintering a "C" shaped layer of an interior wall, tension is created within the wall along the centerline of the wall due to the material shrinking as it cools. The recesses 54 reduce this tension. The recesses break up the tension in the interior wall 18 by separating the interior wall 18 into shorter segments and by providing lateral jogs in the wall where the vertical walls 74 can contract in response to stress. Rather than placing the interior wall in tension across its horizontal length, the interior wall 18 can flex slightly at the flanges 66 to reduce tension. In this manner, the interior wall 18 maintains a high degree of strength in its final configuration while minimizing internal stress during sintering. The solid structure 14 is also made with vertical support walls 74. The vertical support walls 74 are oriented so that they have a minimal contribution to internal stresses present along the length of the interior wall 18. The vertical support walls 74 do not add significant internal stresses to the porous implant because they do not have significant continuous horizontal sections in any particular layer of the construct and are not aligned with the interior wall 18. In each layer of the porous implant, the vertical support walls 74 are a small strut extending outwardly from the interior wall 18. This portion of the support wall 74 is short and narrow and has minimal internal stresses as it cools. Because it is not continuous and not aligned with the interior wall 18, it contributes little to the internal stress of the overall construct while bracing the interior wall against warping.

The internal support structures 42 help to manage the stresses from sintering sufficiently to allow the porous implants 10 to be laser sintered without problems. The support structures mitigate the stresses present in the solid portions 14 of the porous implants and strengthen the solid portions 14 without also adding to the internal stresses from sintering. The internal support structures allow the porous implants to be manufactured by powder bed fusion techniques such as laser sintering metal powder without experiencing warping or cracking problems.

The above description of illustrated examples of the present invention, including what is described in the Abstract, are not intended to be exhaustive or to be limitation to the precise forms disclosed. While specific examples of the invention are described herein for illustrative purposes, various equivalent modifications are possible without departing from the broader scope of the present claims. Indeed, it is appreciated that specific example dimensions, materials, etc., are provided for explanation purposes and that other values may also be employed in other examples in accordance with the teachings of the present invention.

What is claimed is:

1. A porous bone repair implant for repairing bone stock at an artificial joint comprising:
    an implant body, the body having a back wall, a first side wall, and a second side wall, and wherein the implant body is curved such that the first and second side walls extend forwards from the back wall, and wherein the implant body comprises a front opening located between opposing side walls and a channel extending vertically through the implant body;
    wherein the implant body comprises a solid structure comprising sintered powder;
    wherein the solid structure comprises an interior wall of the porous bone repair implant;
    wherein the solid structure comprises a horizontal upper surface located at an upper end of the porous bone repair implant;
    wherein the solid structure comprises a support structure which extends outwardly from the interior wall, wherein the support structure comprises support walls which extend upwardly along an outside of the interior wall, and wherein the support structure forms a plurality of openings between the support walls;
    wherein the implant body comprises an open celled porous structure comprising sintered powder which is attached to an exterior surface of the solid structure and which extends outwardly therefrom to form an exterior surface of the porous bone repair implant;
    wherein the porous structure fills the plurality of openings and extends outwardly beyond the support walls; and
    wherein the porous structure comprises a plurality of struts which are connected together at nodes such that the plurality of struts define a plurality of cells therebetween with openings between adjacent cells.

2. The porous bone repair implant of claim 1, wherein the implant body comprises a vertical height between the upper end and a lower end located opposite the upper end, wherein the channel extends between the upper end and the lower end, and wherein the back wall and the side walls taper inwardly along the vertical height such that the back wall and the side walls are narrower at the lower end of the porous bone repair implant than at the upper end of the porous bone repair implant.

3. The porous bone repair implant of claim 1, wherein the implant body comprises a vertical height between the upper end and a lower end located opposite the upper end, wherein the channel extends between the upper end and the lower end, and wherein the first and second side walls of the implant body each comprise a slot which extends transversely through an upper portion of the side wall between the channel and an outer surface of the implant body and wherein the slot is open through the upper surface of the porous bone repair implant.

4. The porous bone repair implant of claim 1, wherein the interior wall extends along an interior of the back wall and the first and second side walls between the upper end and a lower end located opposite the upper end, and wherein the channel is defined at least in part by the interior wall.

5. The porous bone repair implant of claim 1, wherein the solid structure horizontal upper surface extends horizontally outwardly from the interior wall to form a horizontal upper wall and wherein the support walls are attached to an exterior surface of the interior wall and to a lower surface of the upper wall.

6. The porous bone repair implant of claim 1, wherein the interior wall extends along an interior of the back wall and the first and second side walls and wherein the interior wall comprises a step which extends outwardly away from the channel and forms a recess in the interior wall which is offset away from the channel relative to a portion of the interior wall surrounding the recess.

7. The porous bone repair implant of claim 1, wherein the back wall, the first side wall, and the second side wall comprise an interior surface adjacent the channel and an exterior surface opposite the channel and wherein the porous structure is located at the exterior surface of the back wall, the first side wall, and the second side wall.

8. The porous bone repair implant of claim 1, wherein the support structure comprises support walls which extend upwardly along an outside of the interior wall at an acute angle relative to the upper surface of the porous bone repair implant.

9. The porous bone repair implant of claim 1, wherein the support structure comprises a plurality of first support walls which extend upwardly along an outside of the interior wall at an acute angle relative to the upper surface of the porous bone repair implant and a plurality of second support walls which extend upwardly along an outside of the interior wall at an acute angle relative to the upper surface of the porous bone repair implant, and wherein first support walls cross second support walls and thereby define openings located between the first support walls, the second support walls, and the interior wall.

10. The porous bone repair implant of claim 1, wherein the porous structure forms about 75 percent of the porous bone repair implant by volume.

11. The porous bone repair implant of claim 1, wherein the side walls curve forwards from the back wall such that the implant has a "C" shape when viewed from above.

12. The porous bone repair implant of claim 1, wherein the channel tapers vertically between the upper end and a lower end located opposite the upper end such that a top of the channel is larger in size than a bottom of the channel.

13. The porous bone repair implant of claim 1, wherein the interior wall comprises a plurality of horizontal steps which extend inwardly into the channel.

14. A porous bone repair implant for repairing bone stock at an artificial joint comprising:
- an implant body comprising an upper end, a lower end opposite the upper end, a back wall extending between the upper end and the lower end, a first side wall extending between the upper end and the lower end, and a second side wall extending between the upper end and the lower end, wherein the implant body is curved such that the first side wall and the second side wall extend forwards from the back wall;
- wherein the implant body comprises a front opening located between the first side wall and the second side wall and a channel extending vertically through the implant body between the upper end and the lower end, wherein the back wall, the first side wall, and the second side wall comprise an interior side located adjacent the channel such that the channel is bounded by the interior side of the back wall, the first side wall, and the second side wall, and wherein the back wall, the first side wall, and the second side wall comprise an exterior side which is located opposite the interior side away from the channel;
- wherein the implant body comprises a solid structure comprising fused powder particles;
- wherein the solid structure comprises an interior wall which extends vertically between the upper end and the lower end, which is disposed adjacent the channel and which extends around the channel through the back wall, the first side wall, and the second side wall;
- wherein the solid structure comprises a horizontal upper surface located at the upper end of the porous bone repair implant;
- wherein the solid structure comprises a support structure which extends from the interior wall;
- wherein the implant body comprises an open celled porous structure comprising fused powder particles which is attached to the solid structure interior wall on a side of the interior wall opposite the channel and wherein the porous structure extends outwardly from the exterior surface of the solid structure interior wall in a direction away from the channel to form an exterior surface of the porous bone repair implant;
- wherein the porous structure comprises a plurality of struts which are connected together at nodes such that the plurality of struts define a plurality of cells therebetween with openings between adjacent cells.

15. The porous bone repair implant of claim 14, wherein the solid structure comprises recesses which are formed by the support structure and the interior wall and wherein the porous structure fills the recesses.

16. The porous bone repair implant of claim 14, wherein the support structure extends outwardly from the interior wall away from the channel and wherein the porous structure covers the support structure.

17. The porous bone repair implant of claim 14, wherein the support structure comprises support walls which are attached to an outside side of the interior wall opposite the channel and extend upwardly along the interior wall.

18. The porous bone repair implant of claim 17, wherein the support structure comprises a plurality of first support walls disposed at an acute angle relative to the upper wall and a plurality of second support walls disposed at an acute angle relative to the upper wall, wherein first support walls cross second support walls and thereby define openings located between the first support walls, the second support walls, and the interior wall.

19. The porous bone repair implant of claim 14, wherein the support structure comprises a horizontal wall which extends horizontally from an upper portion of the interior wall, and wherein the support structure comprises support walls which are attached to a lower surface of the upper wall and which are attached to a side surface of the interior wall.

20. The porous bone repair implant of claim 14, wherein the interior wall is located at the interior side of the back wall, first side wall, and second side wall and defines a perimeter of the channel.

21. The porous bone repair implant of claim 14, wherein the first side wall and the second side wall curve forwards from the back such that the implant has a "C" shape when viewed from the upper end.

22. A porous bone repair implant for repairing bone stock at an artificial joint comprising:
- an implant body comprising an upper end, a lower end opposite the upper end, a back wall, a first side wall, and a second side wall which are oriented vertically between the upper end and the lower end, wherein the implant body is curved such that the first and second side walls extend forwards from the back wall, wherein the implant body comprises a front opening located between an end of the first side wall and an end of the second side wall, and wherein the implant body comprises a channel extending vertically through the implant body between the upper end and the lower end, wherein the channel is open to the front opening, and wherein the channel is bounded by inner sides of the back wall, the first side wall, and the second side wall;
- wherein the implant body comprises a solid structure comprising sintered powder;
- wherein the solid structure comprises an interior wall which extends through the back wall, the first side wall, and the second side wall;
- wherein the solid structure comprises a horizontal upper surface located at an upper end of the porous bone repair implant;
- wherein the solid structure comprises a support structure which extends outwardly from the interior wall;

wherein the implant body comprises an open celled porous structure comprising sintered powder which is attached to the interior wall on a side of the interior wall opposite the channel and which extends outwardly from the interior wall to form an exterior surface of the porous bone repair implant;

wherein the porous structure comprises a plurality of struts which are connected together at nodes such that the plurality of struts define a plurality of cells therebetween with openings between adjacent cells.

23. The porous bone repair implant of claim 22, wherein the implant is sized and shaped for use such that, when the implant is installed into a bone the implant body is located inside of the bone, the upper end of the implant is positioned level with a resected surface of the bone, and the porous structure exterior surface is in contact with an interior surface of the bone.

24. The porous bone repair implant of claim 23, wherein, when the implant is installed into a bone, the channel is aligned with a longitudinal axis of the bone.

25. The porous bone repair implant of claim 22, wherein the solid structure comprises a horizontal upper wall disposed at the upper end of the implant body and wherein the support structure comprises support walls which are attached to the interior wall and to a lower surface of the upper wall.

26. The porous bone repair implant of claim 22, wherein the support structure comprises a plurality of support walls which intersect other support walls and form a plurality of recesses between the vertical wall and the support walls, and wherein the porous structure fills the plurality of recesses.

27. The porous bone repair implant of claim 22, wherein the support structure comprises a plurality of first support walls disposed at an acute angle relative to the upper wall and a plurality of second support walls disposed at an acute angle relative to the upper wall, wherein first support walls cross second support walls and thereby define openings located between the first support walls, the second support walls, and the interior wall, and wherein the porous structure fills the openings.

28. The porous bone repair implant of claim 22, wherein the first side wall comprises a first generally vertical slot which extends transversely through an upper portion of the first side wall, which is open through the interior surface of the first side wall to the channel and through the exterior surface of the first side wall, and which is open through the upper end of the implant body, and wherein the second side wall comprises a second generally vertical slot which extends transversely through an upper portion of the second side wall, which is open through the interior surface of the second side wall to the channel and through the exterior surface of the second side wall, and which is open through the upper end of the implant body.

29. The porous bone repair implant of claim 22, wherein the interior wall includes first sections which extend circumferentially around the channel and second sections which extend perpendicular to the channel, and wherein the first sections and the second sections define openings in the interior wall.

\* \* \* \* \*